(12) United States Patent
Raymond et al.

(10) Patent No.: US 7,988,293 B2
(45) Date of Patent: Aug. 2, 2011

(54) METHOD OF QUALIFYING LIGHT SPOTS FOR OPTICAL MEASUREMENTS AND MEASUREMENT INSTRUMENT EMPLOYING METHOD OF QUALIFYING LIGHT SPOTS

(75) Inventors: Thomas D. Raymond, Edgewood, NM (US); John G. Dixson, Albuquerque, NM (US); Stephen W. Farrer, Albuquerque, NM (US); Wei Xiong, Albuquerque, NM (US); Daniel R. Neal, Tijeras, NM (US)

(73) Assignee: AMO Wavefront Sciences LLC., Santa Ana, CA (US)

( * ) Notice: Subject to any disclaimer, the term of this patent is extended or adjusted under 35 U.S.C. 154(b) by 9 days.

(21) Appl. No.: 12/607,368

(22) Filed: Oct. 28, 2009

(65) Prior Publication Data
US 2010/0123873 A1    May 20, 2010

Related U.S. Application Data

(60) Provisional application No. 61/114,978, filed on Nov. 14, 2008, provisional application No. 61/157,496, filed on Mar. 4, 2009, provisional application No. 61/157,497, filed on Mar. 4, 2009, provisional application No. 61/163,858, filed on Mar. 26, 2009.

(51) Int. Cl.
*A61B 3/10* (2006.01)
(52) U.S. Cl. ......... 351/221; 351/212; 351/246; 356/341
(58) Field of Classification Search .................. 351/205, 351/210, 212, 213, 215, 246, 247, 221; 356/337, 356/338, 341, 343, 432, 445
See application file for complete search history.

(56) References Cited

U.S. PATENT DOCUMENTS

| | | | |
|---|---|---|---|
| 4,159,867 A | 7/1979 | Achatz et al. | |
| 4,312,574 A | 1/1982 | Wilms | |
| 4,420,228 A | 12/1983 | Humphrey | |
| 4,440,477 A | 4/1984 | Schachar | |
| 4,530,579 A | 7/1985 | Hyde | |

(Continued)

FOREIGN PATENT DOCUMENTS

JP    11164816 A    6/1999

(Continued)

OTHER PUBLICATIONS

Ming Wang MD, PhD., Corneal Topography in the Wavefront ERA: A Guide to Clinical Application; Chapter 4, Topographic Technologies; Slack Incorporated, 2006.

(Continued)

*Primary Examiner* — Huy K Mai

(57) ABSTRACT

A method of determining a wavefront of a received light beam includes: (a) receiving a light beam; (b) producing a group of light spots from the light beam; (c) qualifying a set of the light spots for use in determining a wavefront of the received light beam; and (d) determining the wavefront of the received light beam using the qualified set of light spots. Qualifying the set of light spots includes, for each light spot: calculating a first calculated location of the light spot using a first calculation algorithm; calculating a second calculated location of the light spot using a second calculation algorithm; and when a difference between the first and second calculated locations for the light spot is greater than an agreement threshold, excluding the light spot from the set of light spots and/or from being employed in determining the wavefront of the received light beam.

27 Claims, 30 Drawing Sheets

U.S. PATENT DOCUMENTS

| | | | |
|---|---|---|---|
| 4,569,576 | A | 2/1986 | Karpov et al. |
| 4,588,270 | A | 5/1986 | Tamaki |
| 4,662,730 | A | 5/1987 | Outwater et al. |
| 4,666,269 | A | 5/1987 | Nakamura et al. |
| 4,761,071 | A | 8/1988 | Baron |
| 4,902,123 | A | 2/1990 | Yoder, Jr. |
| 4,917,458 | A | 4/1990 | Matsumura |
| 4,993,826 | A | 2/1991 | Yoder, Jr. |
| 4,998,819 | A | 3/1991 | Labinger et al. |
| 5,054,907 | A | 10/1991 | Sklar et al. |
| 5,062,702 | A | 11/1991 | Bille |
| 5,106,183 | A | 4/1992 | Yoder, Jr. |
| 5,110,200 | A | 5/1992 | Snook |
| 5,283,598 | A | 2/1994 | McMillan et al. |
| 5,349,398 | A | 9/1994 | Koester |
| 5,392,079 | A | 2/1995 | Fedorov et al. |
| 5,418,582 | A | 5/1995 | van Saarloos |
| 5,585,873 | A | 12/1996 | Shalon et al. |
| 5,640,962 | A | 6/1997 | Jean et al. |
| 5,684,562 | A | 11/1997 | Fujieda |
| 5,793,468 | A | 8/1998 | Shalon et al. |
| 5,847,804 | A | 12/1998 | Sarver et al. |
| 5,864,383 | A | 1/1999 | Turner et al. |
| 5,873,832 | A | 2/1999 | Maloney et al. |
| 5,886,767 | A | 3/1999 | Snook |
| 5,909,270 | A | 6/1999 | Moser et al. |
| 5,920,373 | A | 7/1999 | Bille |
| 5,953,100 | A | 9/1999 | Sarver et al. |
| 5,993,000 | A | 11/1999 | Kobayashi et al. |
| 6,048,065 | A | 4/2000 | Davis et al. |
| 6,050,687 | A | 4/2000 | Bille |
| 6,059,773 | A | 5/2000 | Maloney et al. |
| 6,079,831 | A | 6/2000 | Sarver et al. |
| 6,116,738 | A | 9/2000 | Rorabaugh |
| 6,120,150 | A | 9/2000 | Sarver et al. |
| 6,129,722 | A | 10/2000 | Ruiz |
| 6,152,565 | A | 11/2000 | Liu et al. |
| 6,234,631 | B1 | 5/2001 | Sarver et al. |
| 6,234,632 | B1 | 5/2001 | Nakao |
| 6,257,723 | B1 | 7/2001 | Sarver et al. |
| 6,299,309 | B1 | 10/2001 | Ruiz |
| 6,305,802 | B1 | 10/2001 | Roffman et al. |
| 6,379,008 | B1 | 4/2002 | Chateau et al. |
| 6,428,168 | B2 | 8/2002 | Sarver et al. |
| 6,447,119 | B1 | 9/2002 | Stewart et al. |
| 6,460,997 | B1 | 10/2002 | Frey et al. |
| 6,467,907 | B1 | 10/2002 | Fujieda et al. |
| 6,511,179 | B1 | 1/2003 | Davis et al. |
| 6,547,393 | B2 | 4/2003 | Ruiz |
| 6,569,154 | B2 | 5/2003 | Campin et al. |
| 6,575,573 | B2 | 6/2003 | Lai et al. |
| 6,592,574 | B1 | 7/2003 | Shimmick et al. |
| 6,601,956 | B1 | 8/2003 | Jean et al. |
| 6,607,273 | B2 | 8/2003 | Sarver et al. |
| 6,610,048 | B1 | 8/2003 | Holladay et al. |
| 6,616,275 | B1 | 9/2003 | Dick et al. |
| 6,634,752 | B2 | 10/2003 | Curatu |
| 6,666,857 | B2 | 12/2003 | Smith |
| 6,685,320 | B2 | 2/2004 | Hirohara et al. |
| 6,692,126 | B1 | 2/2004 | Xie et al. |
| 6,705,729 | B2 | 3/2004 | Piers et al. |
| 6,755,528 | B2 | 6/2004 | Isogai |
| 6,848,790 | B1 | 2/2005 | Dick et al. |
| 6,905,210 | B2 | 6/2005 | Applegate et al. |
| 6,913,358 | B2 | 7/2005 | Almeida et al. |
| 6,926,408 | B2 | 8/2005 | Sarver |
| 7,044,944 | B2 | 5/2006 | Campin et al. |
| 7,146,983 | B1 | 12/2006 | Hohla et al. |
| 7,241,012 | B2 | 7/2007 | Mihashi et al. |
| 7,325,927 | B2 | 2/2008 | Applegate et al. |
| 7,394,595 | B2 * | 7/2008 | Somani et al. ............ 359/619 |
| 7,425,067 | B2 * | 9/2008 | Warden et al. ............ 351/205 |
| 2003/0063257 | A1 * | 4/2003 | Molebny ................... 351/212 |
| 2003/0169403 | A1 | 9/2003 | Curatu |
| 2004/0021826 | A1 | 2/2004 | Sarver et al. |
| 2004/0066489 | A1 | 4/2004 | Benedikt et al. |
| 2006/0152677 | A1 | 7/2006 | Youssefi et al. |
| 2006/0209256 | A1 | 9/2006 | Beyerlein et al. |
| 2007/0171365 | A1 | 7/2007 | Tuan |
| 2008/0018910 | A1 | 1/2008 | Neal et al. |

FOREIGN PATENT DOCUMENTS

| | | |
|---|---|---|
| MX | PA01010791 A | 4/2003 |
| WO | WO-03042649 A2 | 5/2003 |
| WO | 03063695 A1 | 8/2003 |
| WO | 03077740 A1 | 9/2003 |

OTHER PUBLICATIONS

Yobani Mejia-Barbosa & Daniel Malacara-Hernandez; Object Surface for Applying a Modified Hartmann test to Measure Corneal Topography; Applied Optics/vol. 40, No. 31/Nov. 1, 2001.

Victor Arni D. P. Sicam et al., Corneal Surface Reconstruction Algorithm that uses Zernike Polynomial Representation; 2004 Optical Society of America; J. Opt. Soc. AM. A/vol. 21, No. 7/Jul. 2004.

Thomas O. Salmon, O.D., Corneal Contribution to the Wavefront Aberration of the Eye; University Graduate School, Nov. 1999.

Juergen H. Massig et al., Videokeratoscope for accurate and detailed measurement of the cornea surface; 2005 Optical Society of Americal Apr. 20, 2005/vol. 44, No. 12/Applied Optics.

J. Rubinstein et al., Reconstruction of Optical Surfaces from Ray Data; Department of Mathmatics, Techion-Isreal Inst. of Technology, Techion City, Hafia; Optical Review vol. 8, No. 4 (2001) 281-283.

Yobani Mejia-Barbosa, Correlation-based method for comparing and reconstructing nearly identical two-dimensional structures; 2001 Optical Society of America, Jan. 10, 2001/vol. 40, No. 2/Applied Optics.

Junzhong Liang et al., Objective measurement of wave aberrations of the human eye with the use of a Hartmann-Shack wave-front sensor; vol. 11/ Jul. 7, 1994/Optical Society of America.

* cited by examiner

METHOD OF QUALIFYING LIGHT SPOTS FOR OPTICAL MEASUREMENTS AND MEASUREMENT INSTRUMENT EMPLOYING METHOD OF QUALIFYING LIGHT SPOTS

CROSS-REFERENCES TO RELATED APPLICATIONS

This patent application claims the priority benefit under 35 U.S.C. §119 from: U.S. provisional patent application 61/114,978 filed on 14 Nov. 2008, in the names of Thomas D. Raymond et al.; U.S. provisional patent application 61/157,496 filed on 4 Mar. 2009, in the names of Thomas D. Raymond et al.; U.S. provisional patent application 61/157,497 filed on 4 Mar. 2009, in the names of Thomas D. Raymond et al.; and U.S. provisional patent application 61/163,858 filed on 26 Mar. 2009, in the names of Thomas D. Raymond et al., the entirety of each of which applications is hereby incorporated herein by reference for all purposes as if fully set forth herein.

BACKGROUND AND SUMMARY

1. Field

This invention pertains to devices and methods for performing optical measurements using a plurality of light spots, and more particularly, to a method of qualifying light spots for use for optical measurements by a measurement instrument, and a measurement instrument employing such a method of qualifying the light spots that are employed in its measurements.

2. Description

There are some devices which employ light spots to make optical measurements. One well-known example is the use of a Shack-Hartmann wavefront sensor.

FIG. 1 illustrates some principal elements of a basic configuration of a Shack-Hartmann wavefront sensor 100. Shack-Hartmann wavefront sensor 100 comprises a micro-optic lenslet array 110 and an optical detector 120. Typically, the optical detector 120 comprises a pixel array, for example, a charge-coupled device (CCD) camera or CMOS array.

The lenslets of the lenslet array 110 dissect an incoming wavefront and create a pattern of light spots 130 that fall onto optical detector 120. In one typical embodiment, lenslet array 110 includes hundreds or thousands of lenslets, each on the size scale of a hundred microns. Meanwhile, optical detector 120 typically comprises many pixels (e.g., 400 pixels) for each lenslet in lenslet array 110. Typically Shack-Hartmann sensor 100 is assembled such that the pixel array 120 lies in the focal plane of lenslet array 110.

Shack-Hartmann wavefront sensor 100 uses the fact that light travels in a straight line to measure the wavefront of light. By sensing the positions of light spots 130, the propagation vector of the sampled light can be calculated for each lenslet of lenslet array 110. The wavefront of the received light can be reconstructed from these vectors.

To better understand one or more aspects of this invention, it is worthwhile to discuss the operation of Shack-Hartmann wavefront sensor 100 in more detail. However, embodiments of the present invention extend to other types of optical measurement devices and systems such as topographers. In certain embodiments of the present invention, a system includes two or more optical measurement devices, for example, a combined system including both a wavefront sensor and a topographer.

In the case of the wavefront sensor 100, some optical system is employed to deliver a wavefront onto lenslet array 110, which samples the wavefront over the tiny regions of each lenslet. Beneficially, the lenslets are much smaller than the wavefront variation. For the purposes of this discussion, we define "isoplanatic" as the condition where the wavefront is well approximated by a plane wave over an area the size of a lenslet. In that case, the wavefront is preferably isoplanatic over the sampled region. When detector array 120 is in the focal plane of lenslet array 110, each lenslet will create a light spot on detector array 120. The location of these light spots reveals the average of the wavefront slopes across each region. That is, the shift in the location of a light spot is proportional to the average of the slope of the wavefront over the region sampled by the corresponding lenslet that produced the light spot. Software may compute the shift in each light spot.

In a typical operation, a reference beam (e.g., a plane wave) is first imaged onto lenslet array 110 and the locations of the resultant light spots ("reference locations") on detector array 120 is recorded. Then, a wavefront of interest is imaged onto lenslet array 110, and the locations of the light spots on detector array 120 produced by the wavefront of interest is recorded and compared against the reference locations.

FIGS. 2A-F illustrate an idealized example of this process where a reference beam and a wavefront of interest are imaged onto a detector array of a wavefront sensor. This idealization shows the process of measuring a spherical wave with a wavefront sensor with just 16 lenslets. The first step, as represented by the FIGS. 2A-2C, is to measure a plane wave and measure the corresponding series of light spot locations 210 which are used as reference locations 220. The next step, as depicted in FIGS. 2D-2F, is to introduce a wavefront of interest and determine the shifts in the locations 240 of the light spots 230 from their reference locations 220.

If the wavefront is not isoplanatic, the quality of the light spot erodes rapidly and it becomes more difficult to determine the location. However, where the isoplanatic condition is satisfied and where the light spot shift is consistent with the small angle approximation of Fresnel, then the light spot shift is exactly proportional to the average of the wavefront slope over the lenslet. The incident wavefront is then reconstructed from the measurements of the average of the slopes for the hundreds or thousands of lenslets in the lenslet array.

Further details regarding the construction and operation of a Shack-Hartmann wavefront sensor and a system for measuring aberrations in an eye using the Shack-Hartman wavefront sensor are described in U.S. Pat. No. 7,122,774, issued on 17 Oct. 2006 to Daniel R. Neal et al., the entirety of which is hereby incorporated by reference for all purposes as if fully set forth herein.

One important application for Shack-Hartmann wavefront sensors is in the field of ophthalmic aberrometry. In common practice, a measurement instrument employing a Shack-Hartmann wavefront sensor injects near infrared light into a patient's eye which focuses on the retina and scatters back toward the instrument. This light is imaged onto the Shack-Hartmann lenslet array, and each lenslet in the lenslet array focuses the local portion of the incident light it intercepts onto the detector array, as described above. Data pertaining to the locations of the light spots is used to derive slope information using a least squares fit method, and thereby to construct the wavefront of the received light. The quality of the fit data, usually evaluated using Zernike coefficients, is affected by the quality of the light spot location data, and every effort is made to ensure the data quality is adequate to the measurement accuracy and precision requirements.

FIG. 3 shows a typical raw image from a wavefront sensor. The nominally rectilinear array of light spots is produced by a rectilinear lenslet array. The detailed analysis of the locations of these light spots relative to their reference locations (i.e., the locations that result when a true plane wave is applied to the lenslet array) yields the local gradient of the incident wavefront. The overall area in which focal spots are present is determined by the patient's pupil, and analysis of this illuminated area yields the location size and shape of the pupil.

The application of Shack-Hartmann wavefront sensors to ophthalmic aberrometry has been a success. However, improvements may be provided by eliminating or reducing the effects of errors that may be caused by complicating factors inherent to the measurement method. Some of the important error sources are illustrated in FIG. 3 and will be described below.

The incident near infrared beam not only scatters from a patient's retina, but also reflects directly from the patient's cornea. The use of a Range Limiting Aperture (RLA) in the measurement instrument, as described in U.S. Pat. No. 6,550,917 issued on 22 Apr. 2003 to Daniel R. Neal et al., can significantly reduce the intensity of the reflected light (U.S. Pat. No. 6,550,917 is hereby incorporated by reference in its entirety for all purposes as if fully set forth herein). However, this so-called "corneal reflex" is generally orders of magnitude brighter than the desired retinally scattered light, and—beneficially—may be excluded from the wavefront calculations. Indeed, as is illustrated by reference numeral 310 in FIG. 3, the reflex can affect a neighborhood of nearby focal spots by introducing stray light that can alter the true light spot location or mask the light spot entirely. The location and intensity of the corneal reflex is affected by corneal shape and the actual position of the patient's eye when the data is acquired. For these reasons, the qualification and/or exclusion of light spot data in and around the corneal reflex can be challenging.

The retinal scatter that is necessary for the aberrometer measurement is highly speckled because the retinal structure is quite rough compared to the wavelength of the probe beam. This leads to variability in the relative brightness of the focal spots. A measurement instrument may employ a broadband probe beam to reduce the speckle, but even so, the intensity of the light spots can vary by a factor of four in a normal clear eye. Additional variation can be introduced by cataracts, "floaters" and opaque regions in pathological crystalline lenses. Cataracts diffuse the incident and return beams causing both reduced spot intensity and broader light spots. As a result, as shown in FIG. 3, the raw image from the wavefront sensor may include dim light spots 320 and/or missing light spots 330.

Additional reflections of the probe beam may be produced by each surface in eyes implanted with intraocular lenses (IOLs). While similar to the corneal reflex phenomenon, multiple reflections are typically present in these patients and may be far from the optic axis of the wavefront sensor. Also, in subjects with diffractive IOLs, it is expected that one lenslet focal spot per diffraction order transmitted through the optical system may be present. In some cases this will lead to two or more focal spots that may or may not be spatially separated. Such focal spot distributions can lead to inaccurate spot location and therefore inaccurate wavefront measurements.

Another source of error in wavefront measurements is tear film breakup. Tear film break up can affect the location and sharpness of the light spots in the vicinity of the breakup. Tear film breakup is correlated to delays in blinking the eye. Some measurement systems may be designed to operate rapidly and reduce tear film breakup effects by avoiding the need to keep the patient from blinking for long periods. Nevertheless, it is still possible that light spots are affected by tear film breakup. This can negatively impact the resultant wavefront measurements.

The spot location algorithms used with a typical wavefront measurement instrument are designed to work with data taken within the nominal linear range of the detector device (e.g., a CMOS detector). Obviously the spot location information is compromised when the spot brightness is poor compared to stray light and camera noise. As described in U.S. Pat. No. 6,550,917, a wavefront measurement instrument may employ a dynamic range limiting aperture (RLA) to significantly enhance its immunity to stray light. However some environmental factors may lead to increased stray light levels; e.g., pointing the system toward a bright light source. A wavefront measurement instrument may incorporate high quality digital CMOS cameras to minimize the effects of camera dark noise. In that case, spots with many pixels that saturate the detector will yield less accurate spot location information.

Therefore, it would be desirable to provide one or more methods of qualifying which light spots are used for optical measurements by a measurement instrument. It would also be desirable to provide a measurement instrument employing a method of qualifying the light spots that are employed in its measurements.

In one aspect of the invention, a method employs an optical sensor to determine a property of an object. The method comprises: (a) illuminating the object with light from one or more light sources; (b) receiving light from the illuminated object; (c) producing a group of light spots from the received light; (d) qualifying a set of the light spots for use in determining a property of the object; and (e) determining the property of the object using the qualified set of light spots. Qualifying the set of light spots includes, for each light spot in the group of light spots: calculating a first calculated location of the light spot using a first calculation algorithm; calculating a second calculated location of the light spot using a second calculation algorithm different from the first calculation algorithm; and when a difference between the first and second calculated locations for the light spot is greater than an agreement threshold, excluding the light spot from the qualified set of light spots. In addition, the light spots excluded from the qualified set may be excluded from being employed in determining the property of the object. Alternatively, one or more of the spots excluded for the qualified set of light spots may be considered for inclusion in a second set of light spots. Some or all of the second set of light spots may also be used in determining the property of the object, for example, by assigning a lower weighting than those spots in the qualified set. Alternately, some or all of the second set of light spots may be used to detect, measure, or characterize some feature of the optical system or eye, e.g., cataracts, tear film conditions, surface anomaly, or the like.

In another aspect of the invention, a device includes: one or more light sources for illuminating an object; a light spot generator adapted to receive light from the illuminated objected and to generate a group of light spots from the light received from the illuminated object; a detector adapted to detect the light spots and for outputting light spot data pertaining to each light spot; and a processor adapted to process the light spot data to determine a property of the object. The processor processes the light spot data by: qualifying a set of the light spots for use in determining the property, and determining the property of the object using the qualified set of light spots. Qualifying the set of light spots includes, for each light spot in the group of light spots: calculating a first calculated location of the light spot from the light spot data using a first calculation algorithm; calculating a second calculated location of the light spot from the light spot data using a second calculation algorithm different from the first calculation algorithm; and when a difference between the first and second calculated locations for the light spot is greater than an agreement threshold, excluding the light spot from the qualified set of light spots. Beneficially, in addition, the light spots excluded from the qualified set of light spots may be excluded from being employed in determining the property of the object.

In yet another aspect of the invention, a method comprises: producing a first set of first light spots from an eye with a corneal topography measurement; producing a second set of second light spots from the eye with a wavefront aberrometry measurement; and qualifying one or more of the light spots within one of the first and second set of light spots based on the other of the first and second set of light spots.

In still another aspect of the invention, a method is provided for determining a condition of an eye. The method comprises: providing a wavefront aberrometer with a first light source and a topographer with a second light source; illuminating an eye with the first light source to produce a first group of light spots; receiving the first group of light spots at a first detector array to produce a first signal containing a first set of data; illuminating the eye with the second light source to produce a second group of light spots; receiving the second group of light spots at a second detector array to produce a second signal containing a second set of data; comparing the first set of data to the second set of data; and based on the comparison, determining an abnormality of the eye.

DETAILED DESCRIPTION

Methods of qualifying light spot data as described below can be employed in a variety of different measurement instruments. Exemplary embodiments will be described in some detail below so as to illustrate various aspects and advantages of these methods. However, it should be understood that the principles involved in these method can be employed in a variety of other measurement instruments which employ light spot data.

Figure 4:
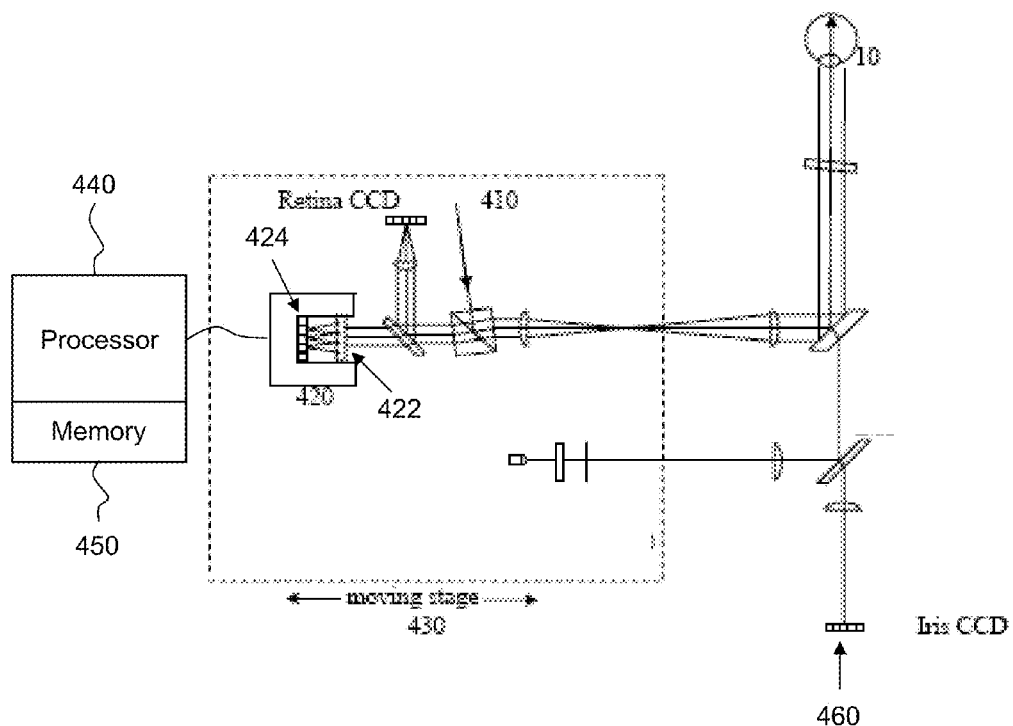
FIG. 4 illustrates one embodiment of a measurement instrument employing a wavefront sensor.

FIG. 4 illustrates one embodiment of a measurement instrument employing a wavefront sensor. In particular, FIG. 4 illustrates a wavefront aberrometer 400 for making wavefront measurements of a subject's eye 100. Among other components, wavefront aberrometer 400 includes a light source 410, a wavefront sensor 420, and other components on a moving stage 430, a processor 440, memory 450 associated with the processor 440, and an iris camera 460. Further details of the construction and operation of wavefront aberrometer 400 can be found in U.S. Pat. No. 7,494,220 issued on 24 Feb. 2009 in the names of Richard Copland et al., the entirety of which is hereby incorporated herein by reference for all purposes as if fully set forth herein.

Figure 1:
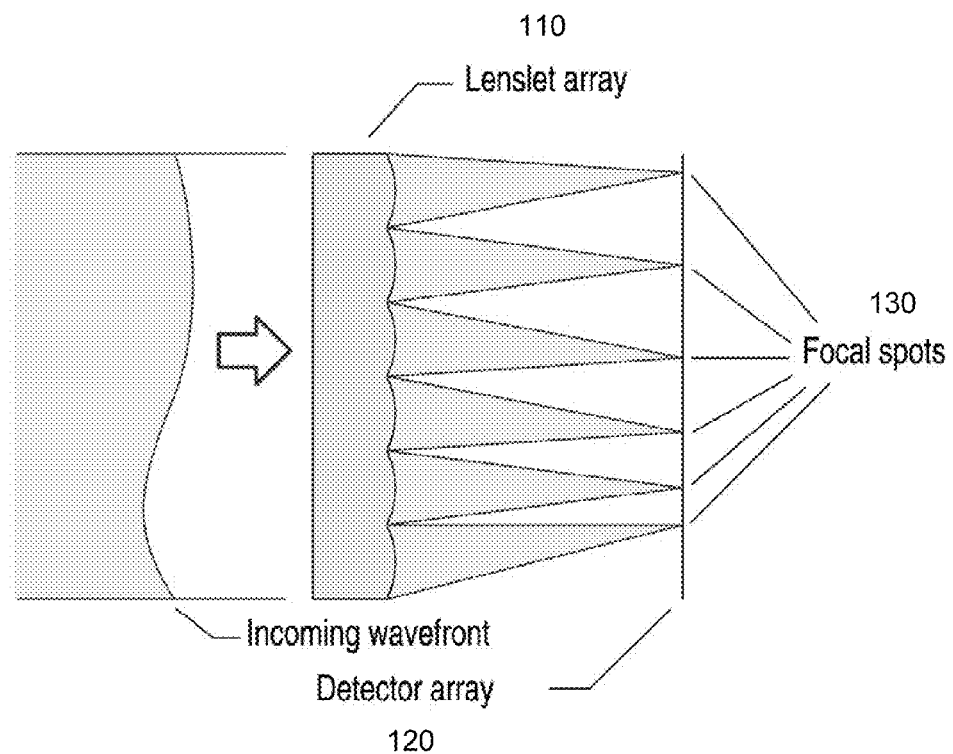
FIG. 1 illustrates some principal elements of a basic configuration of a Shack-Hartmann wavefront sensor.
Figure 2A:
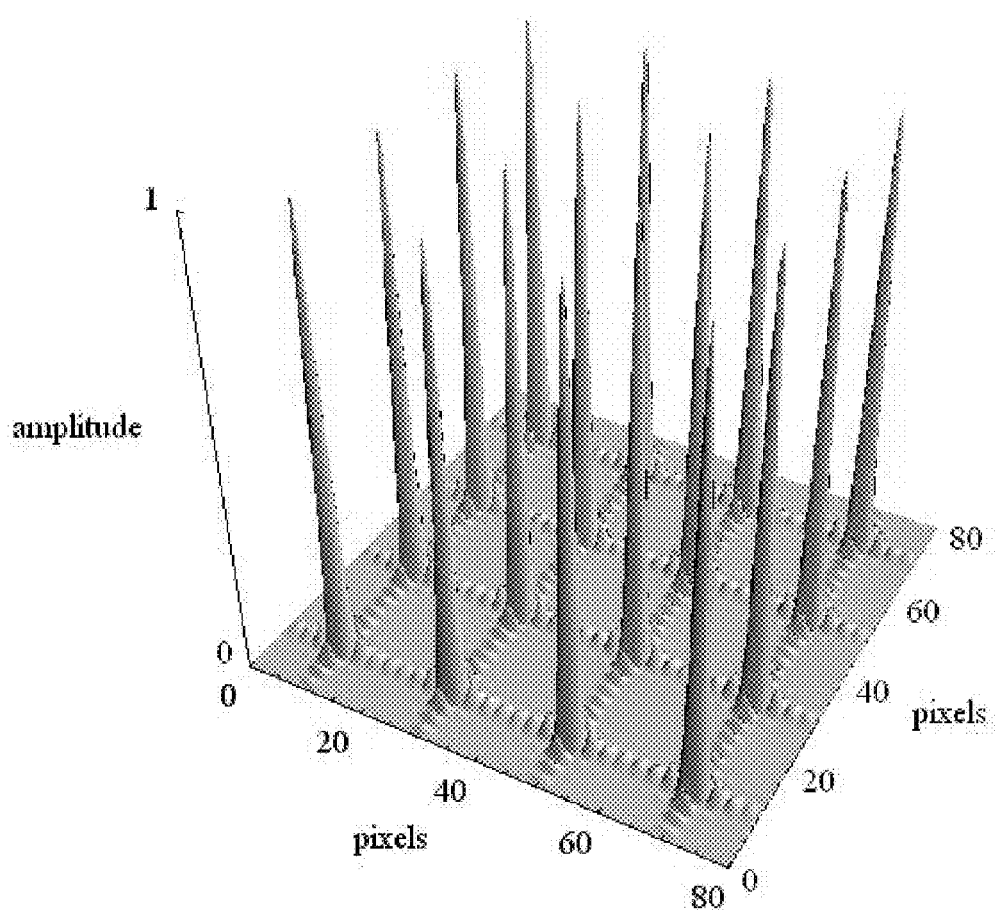
FIGS. 2A-F illustrate a reference beam and a wavefront of interest being imaged onto a detector array of a wavefront sensor.
Figure 2B:
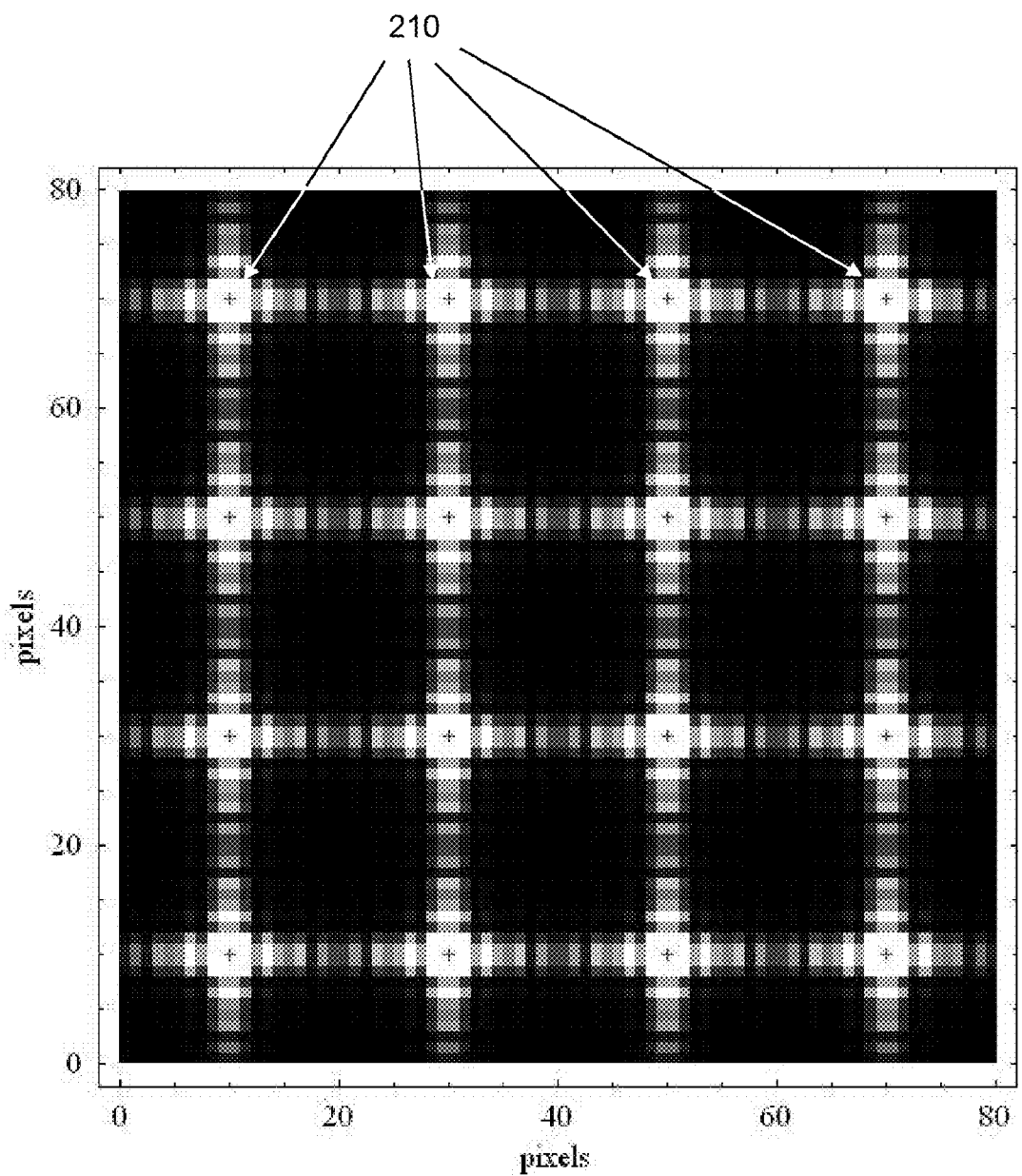
Figure 2C:
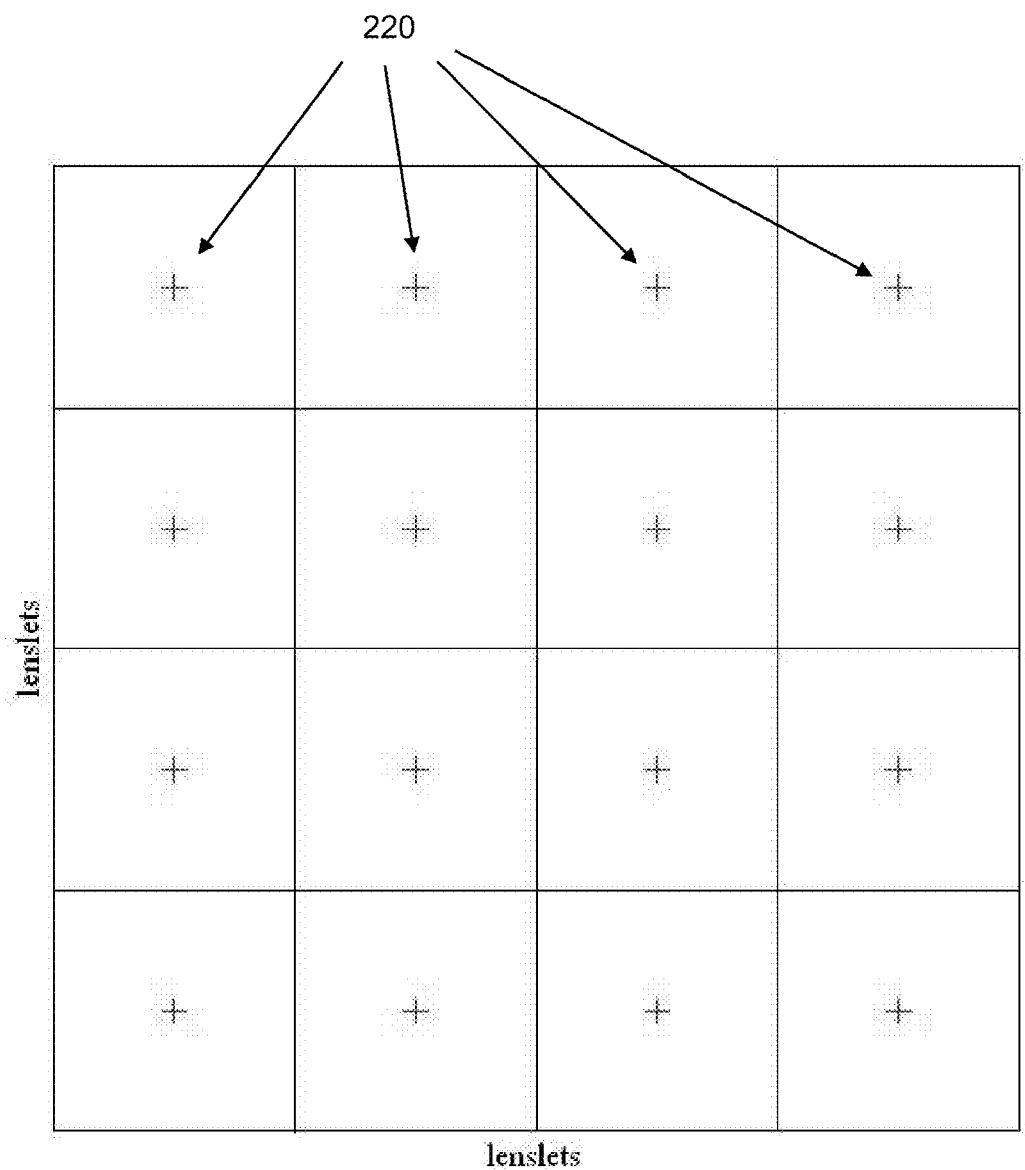
Figure 2D:
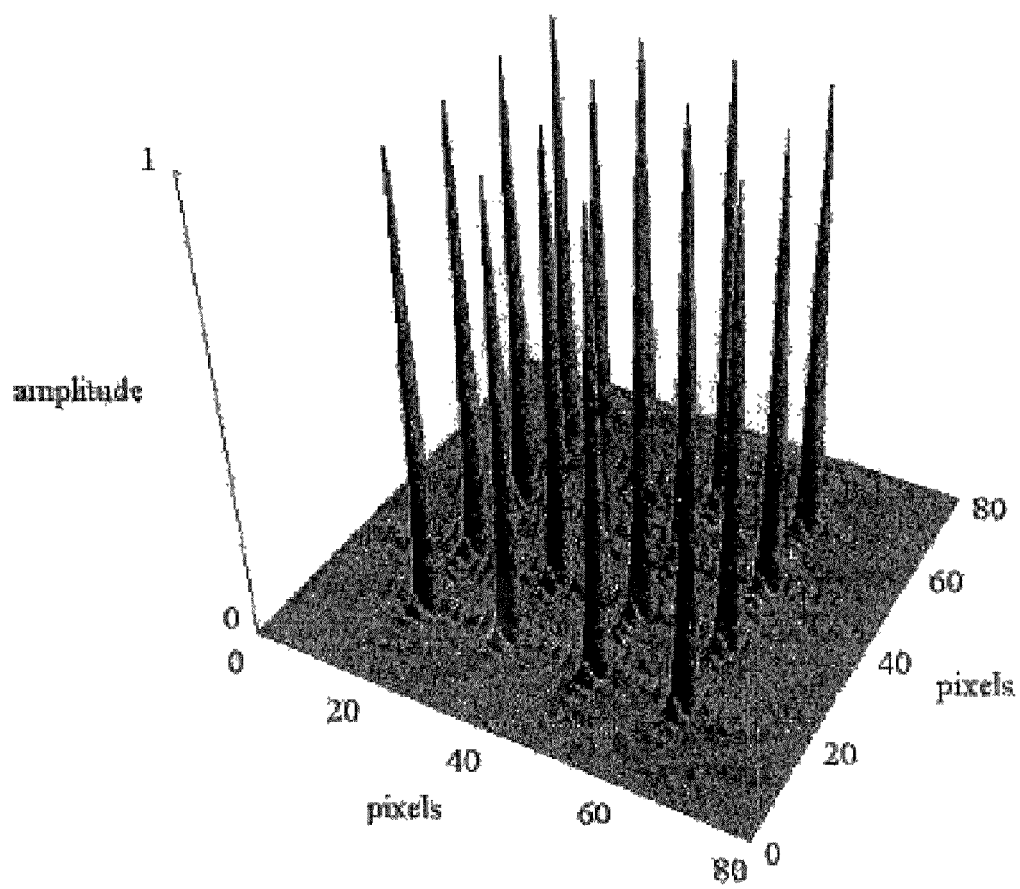
Figure 2E:
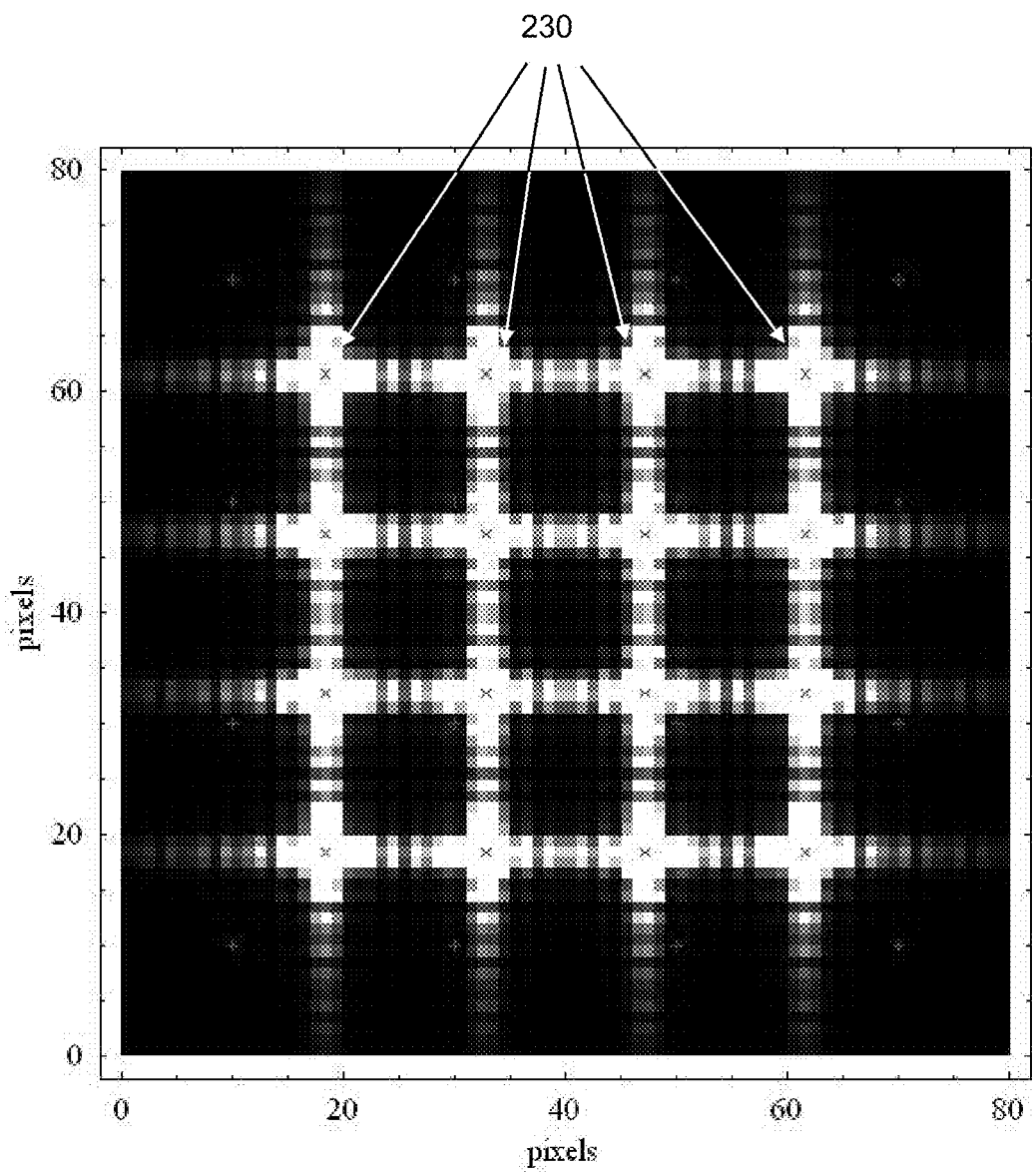
Figure 2F:
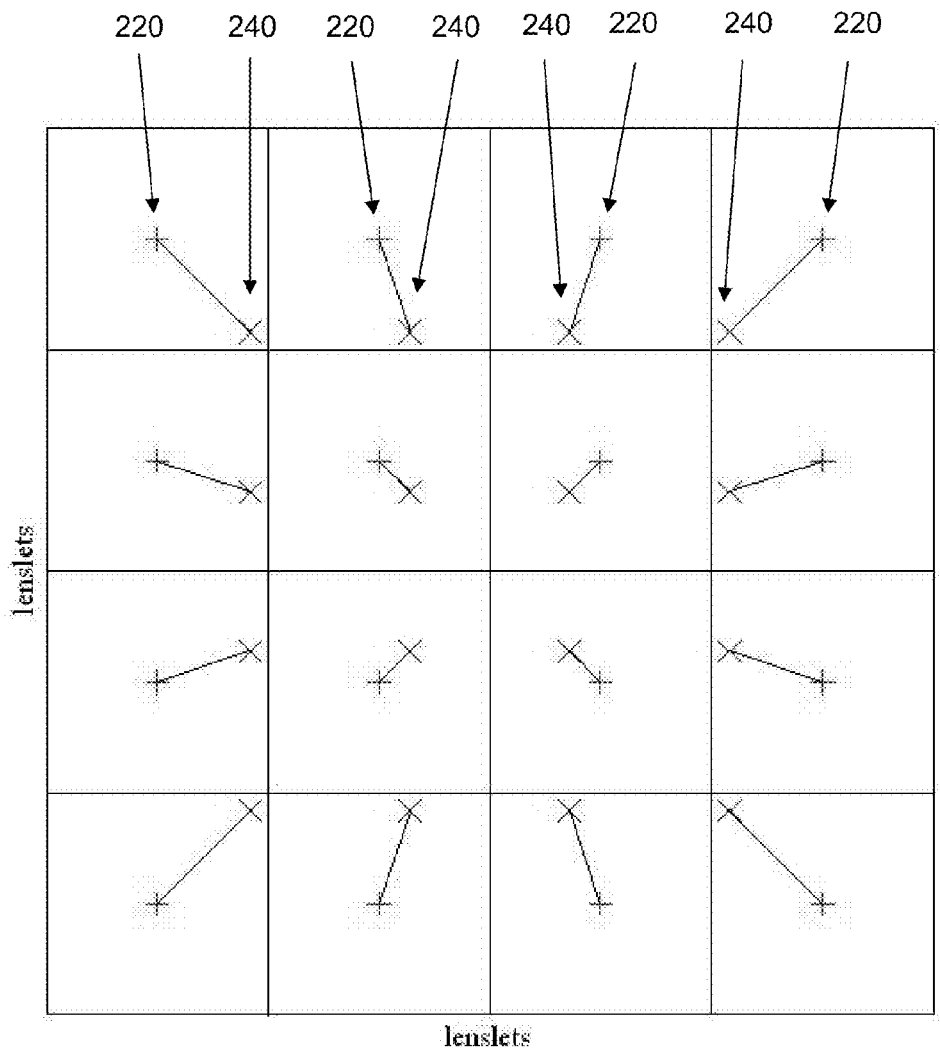

Of particular relevance here, wavefront sensor 420 operates in conjunction with processor 440 and associated memory 450 to perform wavefront measurements on eye 100. Wavefront sensor 420 includes a lenslet array 422 and a detector array 424. Further details of the construction and operation of lenslet array 422 and detector array 424 may be understood with reference to the description of wavefront sensor 100 of FIG. 1 provided above. Light spot data from detector array 424 is supplied to processor 440 and associated memory 450 to execute one or more algorithms to determine a wavefront of a light beam received from the eye 100. Beneficially, processor 440 may perform these algorithms in accordance with instructions stored in memory 450.

Beneficially, processor 440 executes an algorithm to apply certain qualification criteria to light spot data from detector array 424 to determine which of the light spot data is qualified to be employed in determining the wavefront of the light beam from the eye 100, and to exclude light spots that do not meet the qualification criteria. Through such an algorithm, processor 440 may exclude light spots that are of dubious quality such as light spots near the corneal reflex, spots that highly saturate detector array 424, and light spots distorted by cataracts, tear film breakup, or other ocular conditions.

In a particular embodiment, processor 440 qualifies light spots produced by lenslet array 422 and a detector array 424 by performing one or more tests to determine whether the light spot data is believed to have been influenced by extraneous factors such as: corneal reflex: cataracts, "floaters" and opaque regions in the eye; intraocular lenses, tear film breakup; etc., and therefore, beneficially, may be excluded from the set of light spots used for the wavefront calculations.

Beneficially, processor 440 identifies light spots whose location accuracy is compromised by light scattered from the corneal reflex, cataracts, or a tear film condition. In one embodiment, processor 440 qualifies a light spot for inclusion in the wavefront calculations by: calculating a first calculated location of the light spot using a first calculation algorithm; calculating a second calculated location of the light spot using a second calculation algorithm different from the first calculation algorithm; and when a difference between the first and second calculated locations for the light spot is greater than a predetermined agreement threshold, excluding the light spot from the set of light spots and/or from being employed in determining the wavefront of the received light beam. Other light spot qualification criteria may be employed as described in greater detail below.

Figure 5:
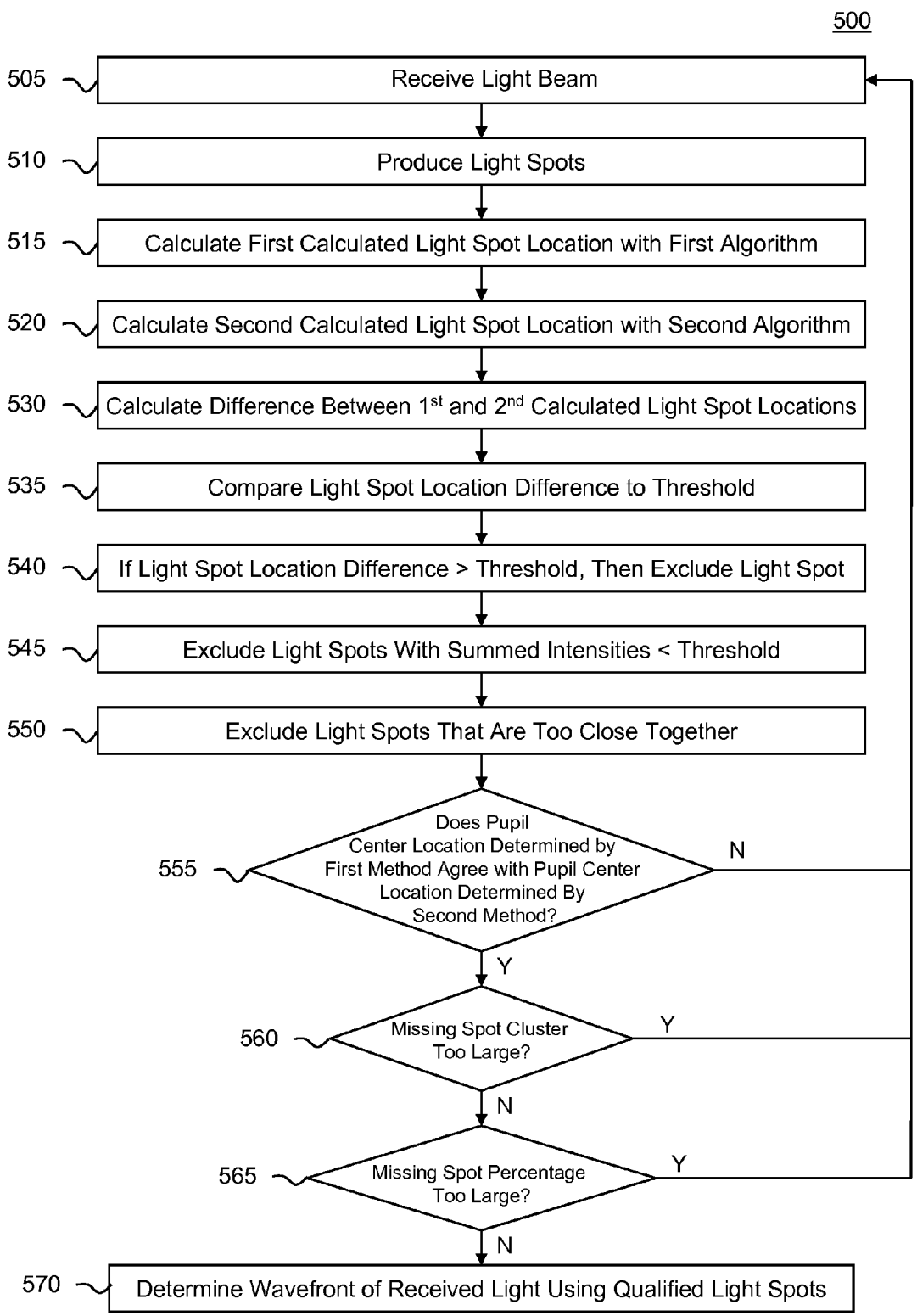
FIG. 5 shows a flowchart illustrating one embodiment of a method of qualifying light spot data for a wavefront measurement.

FIG. 5 shows a flowchart illustrating one embodiment of a method 500 of determining a wavefront of a received light beam by qualifying which light spot data is employed for wavefront the measurements. In one embodiment, method 500 may be performed by a system such as the system 1000 which will be described in greater detail below with respect to FIG. 15.

In a first step 505, a wavefront sensor receives a light beam. In an arrangement such as that shown in FIG. 4, the light beam is received back from the retina of a subject's eye.

In a next step 510, a lenslet array of the wavefront sensor produces a group of light spots from the received light beam and images those light spots onto a detector array.

In a step 515, a processor calculates a first calculated location of each light spot in the group of light spots using a first calculation algorithm. An exemplary embodiment of such a first calculation algorithm will be described below with respect to FIGS. 6A-D.

In a step 520, a processor calculates a second calculated location of each light spot in the group of light spots using a second calculation algorithm that is different from the first calculation algorithm. An exemplary embodiment of such a second calculation algorithm will be described below with respect to FIGS. 7A-D.

In a step 530, the processor calculates a difference between the first and second calculated locations for each light spot in the group.

In a step 535, for each light spot in the group, the processor compares the difference between the first and second calculated locations for the light spot, to a predetermined agreement threshold.

In a step 540, the processor excludes from a qualified set of light spots those light spots where the difference between the first and second calculated locations is greater than the agreement threshold. Beneficially, the qualified set of spots can be employed in determining the wavefront of the received light beam In a step 545, the processor determines a summed intensity value of an assigned group of pixels of the detector array assigned to each light spot, and excludes from the set of qualified light spots those light spots whose summed intensity is less than a predetermined summed intensity threshold. Absolute intensity thresholds which are tested in step 545 insure that light spots are sufficiently bright to yield accurate data. An exemplary embodiment of such algorithm for performing step 545 will be described below with respect to FIG. 12.

In a step 550, the remaining light spots in the qualified set of light spots are checked to insure that each light spot belongs to only one predetermined area of interest (AOI) in the detector array. In one embodiment, the distance between adjacent light spot locations is compared to a minimum distance threshold. In that case if the distance between the adjacent light spot locations is less than the distance threshold, then one or both light spots are excluded from the set of qualified light spots.

In a step 555, an algorithm is employed to insure that the received light beam has not been deleteriously affected by phenomena such as a subject blinking their eye during the measurements, an eyelash blocking part of the light path, etc. In step 555, qualified light spot data is passed to a pupil analysis algorithm to locate the pupil and define its shape and guard against partial blinks. An exemplary embodiment of such an algorithm will be described below with respect to FIGS. 13A-B. When the location of the center of the pupil as determined by a first pupil location determination method differs from the location of the center of the pupil as determined by a second pupil location determination method by more than a pupil location agreement threshold, then the entire set of wavefront data is discarded and the process returns to step 510.

Figure 3:
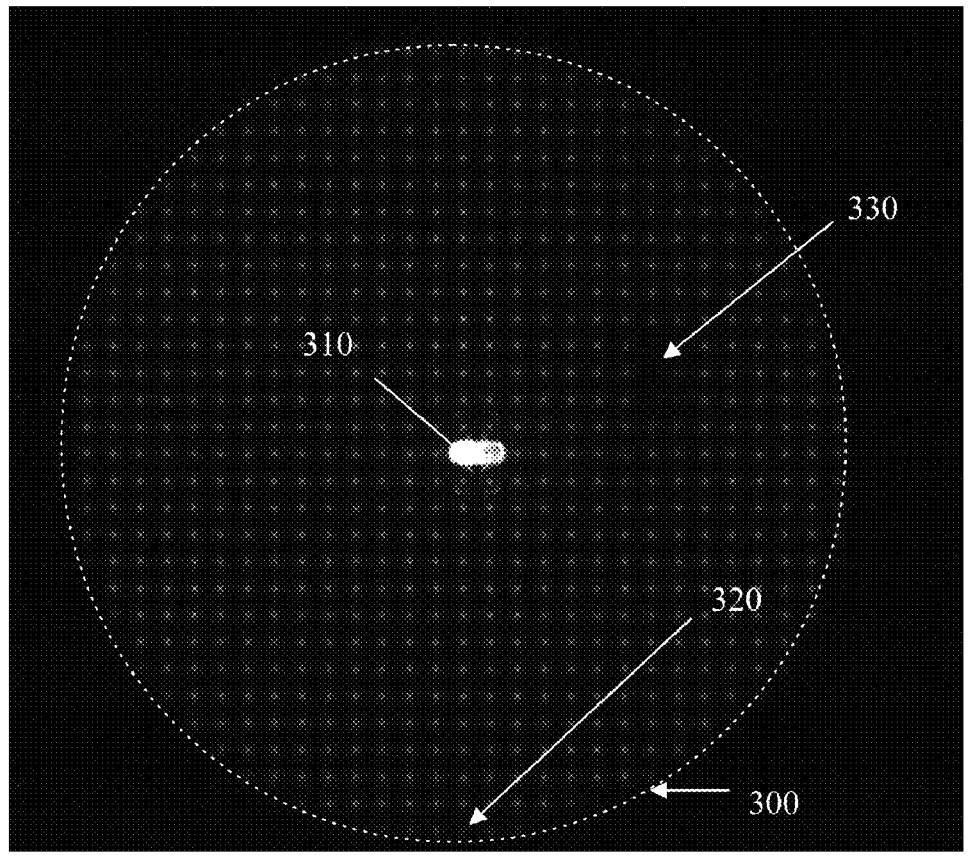
FIG. 3 shows a typical raw image from a wavefront sensor.

In a step 560, the processor determines the size of the largest cluster of connected or adjacent "missing" light spots in the image produced by the lenslet array on the detector array (see missing light spots 330 in FIG. 3) and compares it to a predetermined cluster size threshold (e.g., 21 connected light spots). If the number of connected or adjacent missing light spots is greater than the cluster size threshold, then the entire set of wavefront data is discarded and the process returns to step 510.

Assuming there are N lenslets in the lenslet array that are illuminated by the light beam from the subject's pupil, then ideally there also would be N light spots in the set of qualified light spots. However, as explained above, in general some light spots may be missing, or may be disqualified from the set of qualified light spots based on the criteria applied in one or more of the steps above.

In a step 565, the processor determines the number or percentage of light spots that are missing or disqualified from the set of qualified light spots, and compares the number or percentage to a missing light spot threshold (e.g., 20%). If the percentage exceeds the threshold, then the entire set of wavefront data is discarded and the process returns to step 510.

In steps 555-565, the number of qualified spots within the pupil, the percent fraction of qualified spots within the pupil, and the number of connected disqualified spots may be tallied and compared to the predetermined threshold criteria to qualify the frame of data for wavefront analysis.

In a step 570, the wavefront measurement instrument determines the wavefront of the received light beam using the qualified set of light spots. Beneficially, all missing or disqualified data within the pupil may be interpolated from the qualified light spots. In one embodiment, the qualified light spots are used to determine the local gradients at those respective points. These slope values and positions are used in a Zernike wavefront fit. The coefficients are used to generate slope data at the missing light points.

As described above, method 500 employs two different methods to determine light spot locations and performs a spot by spot cross check on the light spot locations using two or more different light spot location determination methods. A variety of different methods may be employed for determining the locations of the light spots. In some embodiments, intensity-based methods may be employed to determine which pixels to include in the light spot location calculation. In some embodiments, spatially-based methods may use a priori information about what constitutes a "normal" light spot to determine which pixels to include in the light spot location calculation. In some embodiments, correlation based methods are employed using correlation values to determine which pixels to include in the light spot location calculation.

In one beneficial arrangement, both methods calculate the first moments of the light spot minus the background intensity, however the pixels used in the calculations and the background intensity values are determined differently for each method. Beneficially, the selected methods exhibit a high degree of agreement for typical light spot distributions; however they disagree for light spots with pathological distributions. Beneficially, light spots are disqualified whenever the locations from the two methods differ by more than a predetermined agreement threshold. In one embodiment, the agreement threshold is set to one pixel.

In some embodiments, the method 500 may be modified to exclude certain of the steps shown in FIG. 5. For example, the method 500 may be modified to exclude one or more of the exclusion criteria steps 535, 540, 545, and/or 550. Additionally or alternatively, one or more of the steps 555, 560, or 565 may be excluded from the method 500.

In certain embodiments, the method 500 may include additional steps. For example, in addition to, or in place of one of more of the frame qualification tests performed in steps 555-565, an In another example, for the purposes of determining the wavefront, the qualified spots may be assigned a weighting depending on an evaluation criteria (e.g., amount above or below one of the thresholds used in the method 500, or distance from a nearest neighbor). Additionally or alternatively, some or all of the light spots excluded from the set of qualified light spots may be further evaluated or processed. For example, some or all of the excluded light spots may be evaluated for inclusion in a second set of light spots. In such embodiments, the step 570 of method 500 may include the second set of light spots in determining the wavefront, for example, by assigning a reduced weight in calculating the wavefront as compared to the weight or weights given to spots in the qualified set.

Additionally or alternately, the second set of light spots may be used to detect a condition of the optical system or eye (e.g., a cataract condition) and/or form the basis of a qualitative or quantitative characterization of the mechanisms that caused the disqualification. For example, the location and severity of local phase and intensity perturbations caused by cataracts and/or large corneal surface deviation may be measured or estimated based on the second set of light spots.

The method 500 may be adapted or modified for use with other types of input data and/or for making other types of calculations. For example, the light spots may be produced by a corneal topographer, where light reflected from a cornea or other surface are imaged onto a detector to produce a set of light spots that are indicative of a local slope of the cornea or surface. The light spots may be processed using the steps and criteria shown in FIG. 5 and/or using other criteria suitable for evaluating or processing data from gradient measurements located on relatively non-rectangular grids, for example, as disclosed in co-pending U.S. patent application Ser. Nos. 12/347,909 and 12/350,895, the entireties of which are hereby incorporated by reference for all purposes as if fully set forth herein.

It should be understood that the order of the steps illustrated in FIG. 5 could be rearranged in various ways. For example: the order of steps 540, 545 and 550 can be changed; one or more of steps 540, 545 and 550 could be performed before steps 515-535; the order of steps 555 and 560 can be changed; one or more of steps 555 and 560 could be performed before steps 515-535 and/or steps 540, 545 and/or 550; etc.

FIGS. 6A-D illustrate one embodiment of a first method of locating a light spot in a method such as method 500 illustrated in FIG. 5. The method illustrated in FIGS. 6A-D is hereinafter referred to as the "Percent Threshold Method."

The Percent Threshold Method incorporates two parameters: an Irradiance Threshold 610 and a Percent Threshold 620.

The Irradiance Threshold 610 is used to eliminate camera noise and stray light from the data used in the light spot centroid location calculation and is assumed to be constant across the image. In one embodiment, the Irradiance Threshold 610 is nominally set at a value of 30 counts from those pixels of the detector array assigned to each light spot (i.e., the "Area of Interest" or AOI).

The Percent Threshold 620 is used to dynamically threshold the intensity data in proportion to the valid data brightness within the AOI to afford a wide variance in the spot brightness. This is in effect a local threshold that depends on the spot brightness that is crucial for use in instruments where a large variance is in spot brightness or size can be expected; e.g., ophthalmic aberrometers and laser metrology tools. It is generally quite robust against spot brightness but assumes a constant background level, the Irradiance Threshold 610.

The raw intensity values of the pixels within a given AOI are thresholded with a value equal to the Irradiance Threshold 610 plus the product of the Percent Threshold 620 times the brightest intensity minus the Irradiance Threshold 610. The x and y first moments of the pixel data within the AOI are then calculated, as is the sum of the valid intensity, i.e., the sum of the raw intensity values minus the Irradiance Threshold.

Figure 6A:
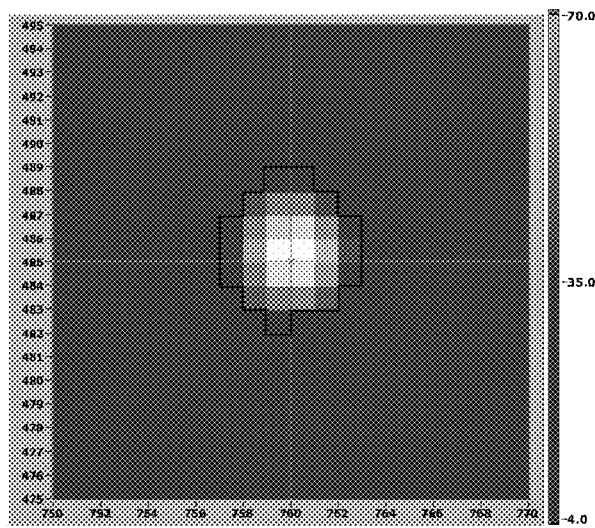
FIGS. 6A-D illustrate one embodiment of a first method of locating a light spot in a wavefront sensor.
Figure 6B:
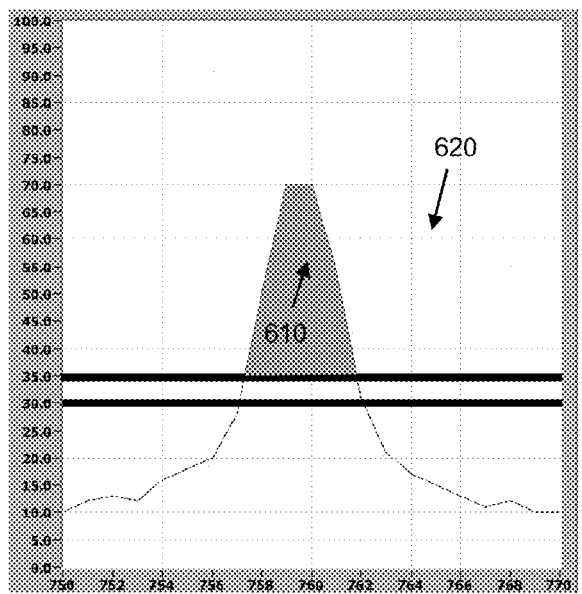
Figure 6C:
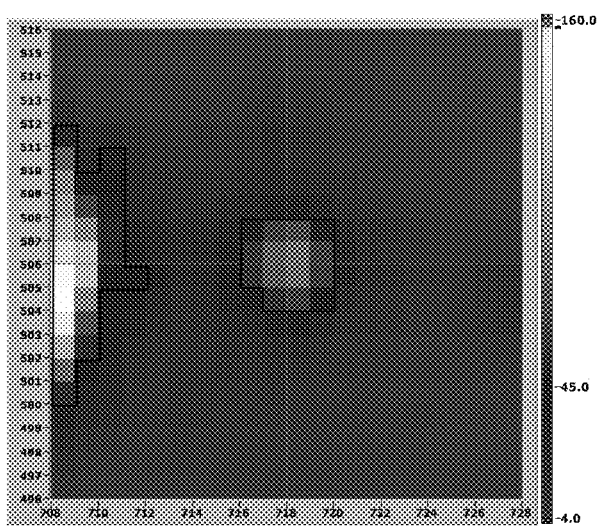
Figure 6D:
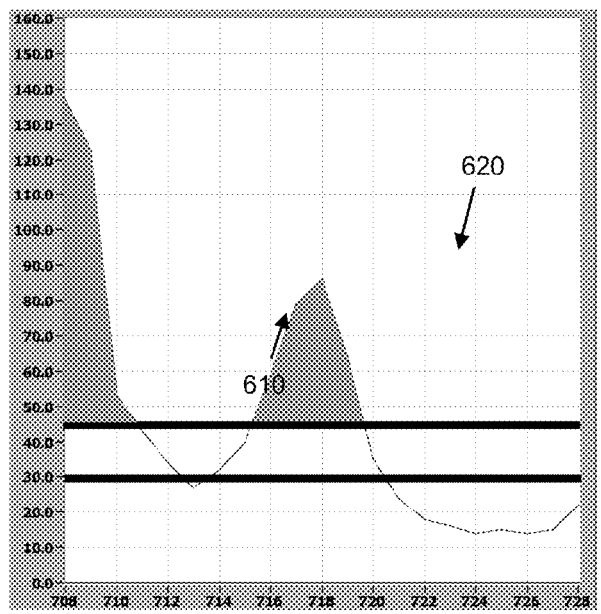
Figure 7A:
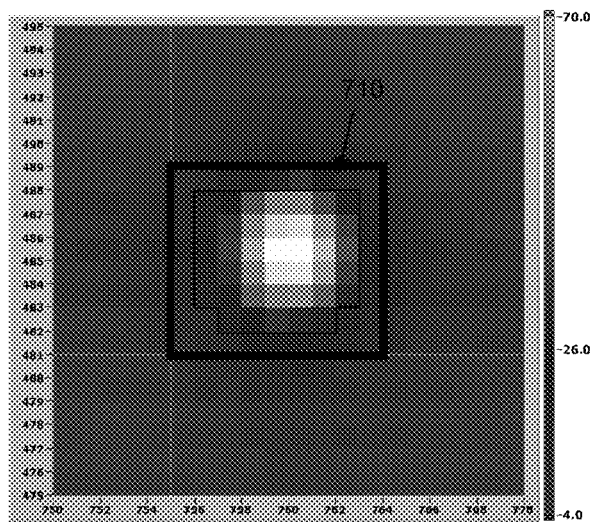
FIGS. 7A-D illustrate one embodiment of a second method of locating a light spot in a wavefront sensor.
Figure 7B:
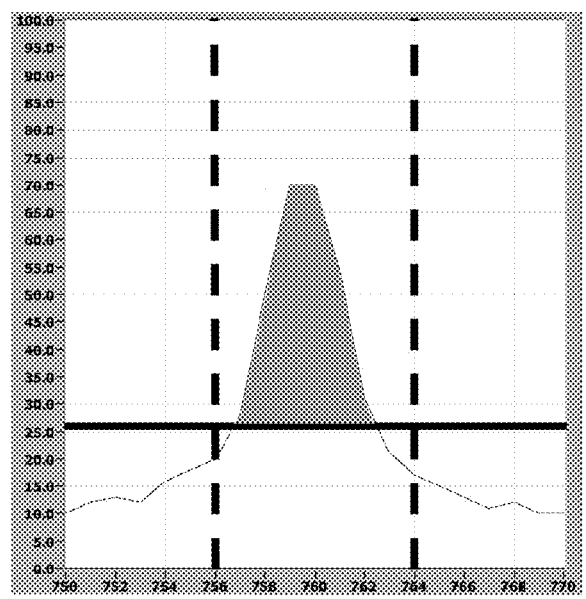
Figure 7C:
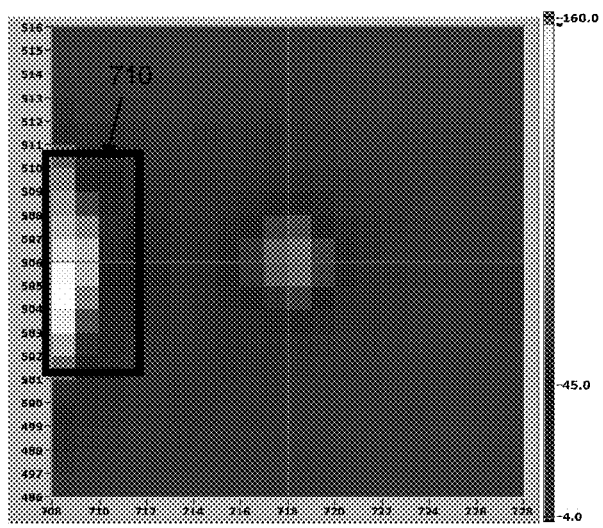
Figure 7D:
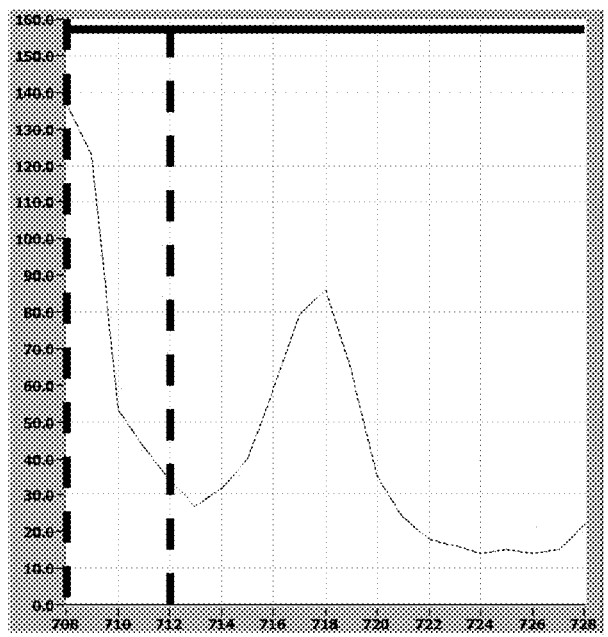

FIGS. 6A-B illustrate a well-formed light spot, and the FIGS. 6C-D show a light spot just to the right of the corneal reflex. FIGS. 6A and 6C show the intensity of the light impinging on the pixels arranged in the x and y directions within the AOI. The pixels in the outlined areas are included in the first moment's calculation. FIGS. 6b and 6D show the intensity distribution in the x direction for determining the x component of the first moment of the intensity distribution within the AOI.

It can be seen from FIG. 6D that the Percent Threshold Method for locating the light spot fails in the case with a light spot just to the right of the corneal reflex.

Accordingly, in one embodiment a first method of locating a light spot comprises: assigning a group of the pixels to the light spot; establishing a pixel intensity threshold for the light spot; determining an intensity value for light received at each pixel in the group; and calculating the first calculated location as a first moment of the pixel intensity values for those pixels whose intensity values are greater than the pixel intensity threshold. Furthermore, in one embodiment, the pixel intensity threshold for the light spot is established by: establishing a background intensity threshold value that is constant for all light spots; determining a maximum intensity value among the intensity values for all of the pixels in the group; establishing a percentage threshold value for the light spot; and establishing the pixel intensity threshold by multiplying the percentage threshold value by the maximum intensity value and subtracting the background intensity threshold value.

FIGS. 7A-D illustrate one embodiment of a second method of locating a light spot in a wavefront sensor. The method illustrated in FIGS. 7A-D is hereinafter referred to as the "Window Method."

The Window Method uses a priori information about the light spot dimensions and the location of the brightest pixel within the AOI to determine which pixels to use in the first moment's calculations, and what background value of light to subtract. In contrast to the Percent Threshold Method which uses local intensity criteria to determine which pixels to include in the first moments calculation, the Window Method uses a spatial criteria and a local background value.

In the Window Method, the raw intensity values of the pixels within a given AOI are reviewed to find the brightest pixel, and a window 710 having predetermined dimensions is centered on the brightest pixel. In a beneficial embodiment, window 710 is a square whose size is sufficiently large to enclose only the primary lobe of the light spot pattern, but considerably smaller than the AOI. In one embodiment, the size of the window 710 is set to nine (9) pixels in each direction. In one embodiment, if the brightest pixel in the AOI is located within one half of the window's length from the edge of the AOI, then the window is truncated at the edge of the AOI. Only pixels within window 710 are used to determine the light spot's location. The intensity values of the pixels along the border of the window are reviewed and the brightest value is used to threshold the intensity of the pixels within window 710. Then the x and y first moments and the sum of the thresholded intensity values for pixels in window 710 are calculated.

Significantly, the Window Method returns a light spot location and intensity of zero whenever the intensity of a pixel on the border of window 710 is equal to the intensity of the brightest pixel in the AOI. This routinely occurs in and around the corneal reflex.

Figure 8A:
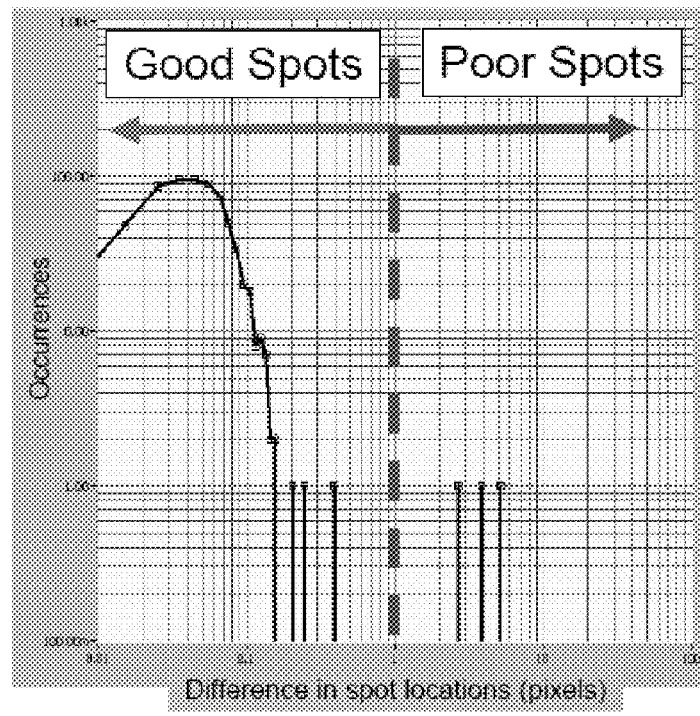
FIGS. 8A-B illustrate differences in the locations of light spots determined by the method of FIGS. 6A-D and locations determined by the method of FIGS. 7A-D for an exemplary image.
Figure 8B:
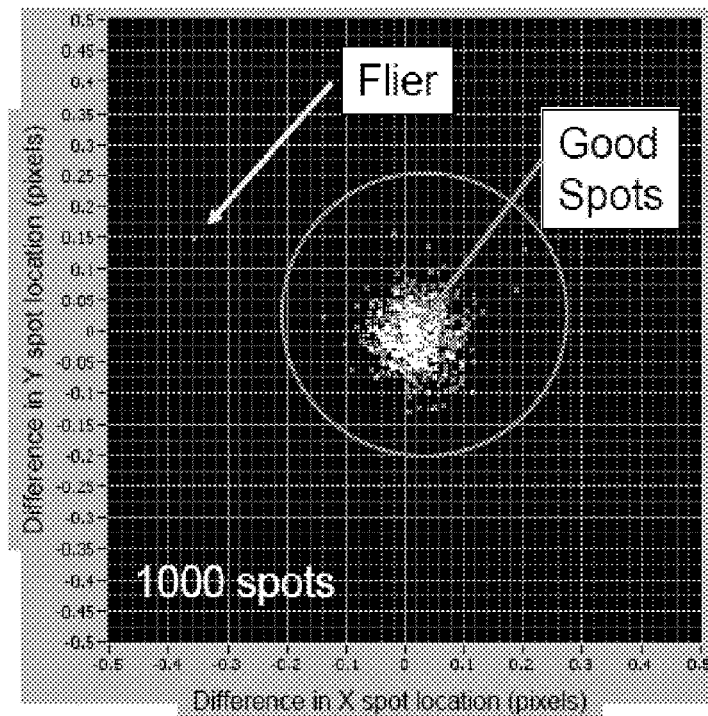

FIGS. 8A-B illustrate differences in the locations of light spots determined by the method of FIGS. 6A-D and locations determined by the method of FIGS. 7A-D for an exemplary image. In particular, FIG. 8A shows an exemplary histogram plot of the differences between the calculated locations of the light spots using the Percent Threshold Method and the calculated locations of the light spots using the Window Method, in pixels, for a bin size equal to 0.01 pixels, FIG. 8B shows the differences for each light spot. The differences for the AOIs that have many fully saturated pixels are of order 100's of pixels and are not shown in FIGS. 8A-B.

In the example illustrated in FIGS. 8A-B, for symmetric, non-saturated light spots on a nominally low and constant background, such as far from the corneal reflex, the Percent Threshold Method and the Window Method produce light spot locations that agree with each other to within a small fraction of a pixel. However, when the light spots are asymmetric, significantly broader than the size of the window employed in the Window Method, reside on a non-uniform or strong background, or are strongly saturated, such as near the corneal reflex, these methods will report spot locations that differ. The differences are typically quite small for well formed light spots, and quite large for pathological light spots. In the example illustrated in FIGS. 8A-B, for well formed light spots, the difference is typically less than 0.1 pixels and for poorly formed light spots it is typically well above one pixel.

Accordingly, in one embodiment, the agreement threshold value is set to 1 pixel, so as to discriminate between well formed light spots and pathological light spots. In that case, light spots whose calculated locations using the Percent Threshold Method and the Window Method disagree by more than the agreement threshold are then disqualified or excluded from being employed in the wavefront calculations.

Figure 9:
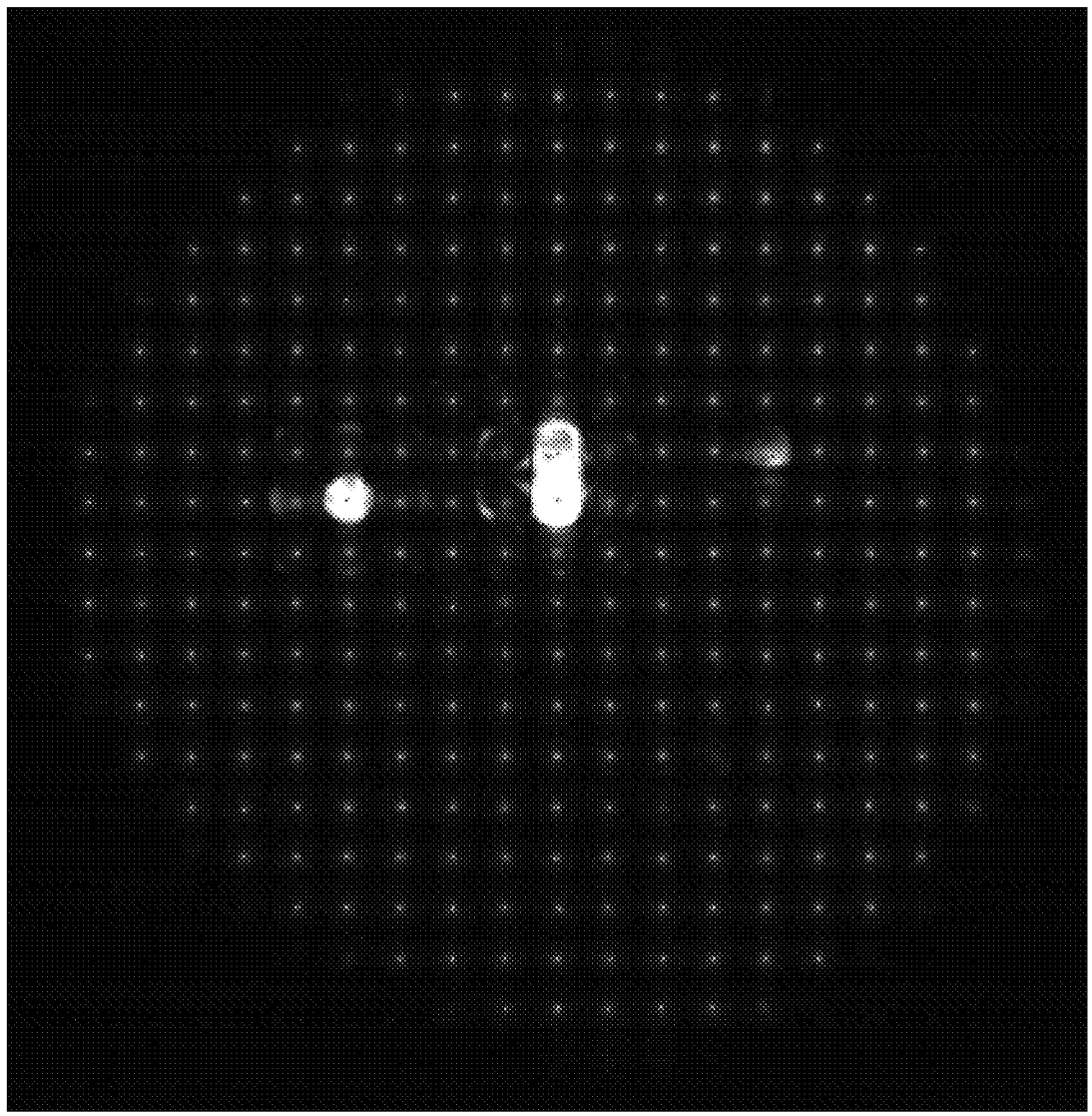
FIG. 9 shows a raw image from a wavefront sensor for a subject with an intraocular lens.
Figure 10:
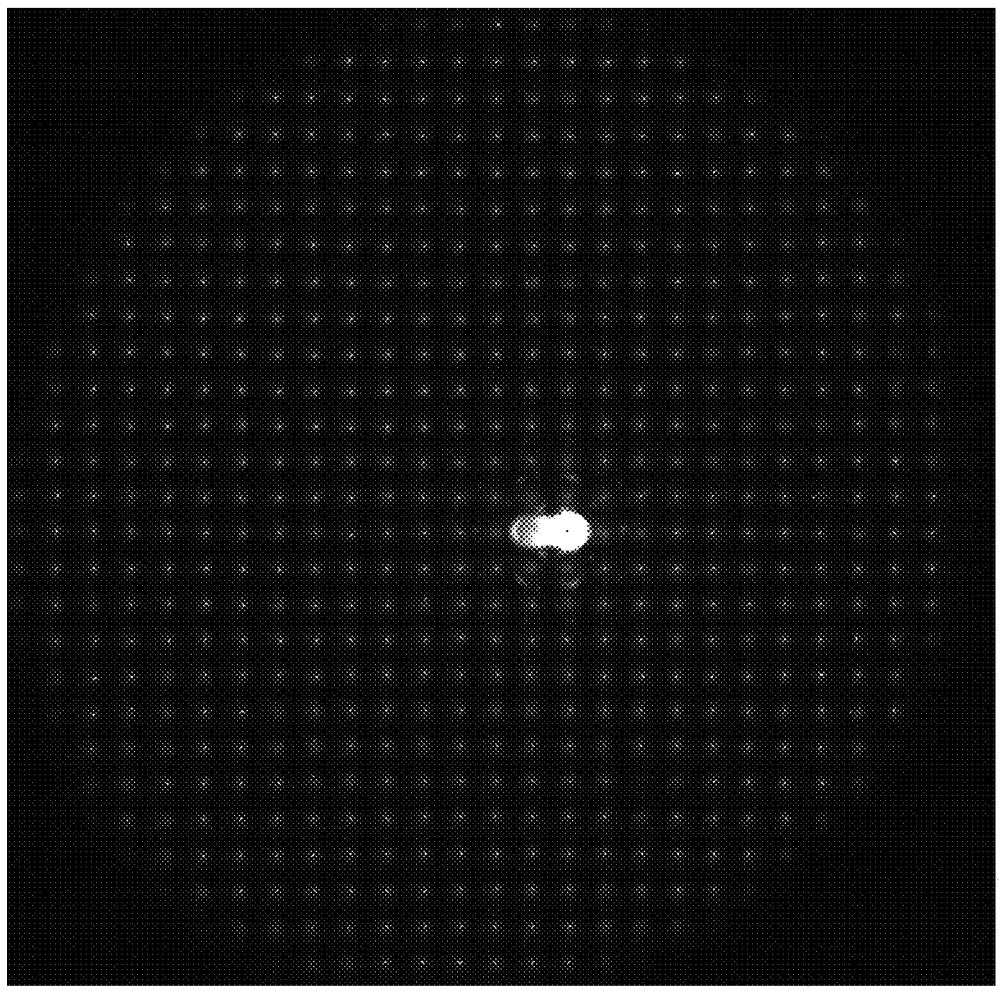
FIG. 10 shows a raw image from a wavefront sensor for a subject with cataracts.
Figure 11:
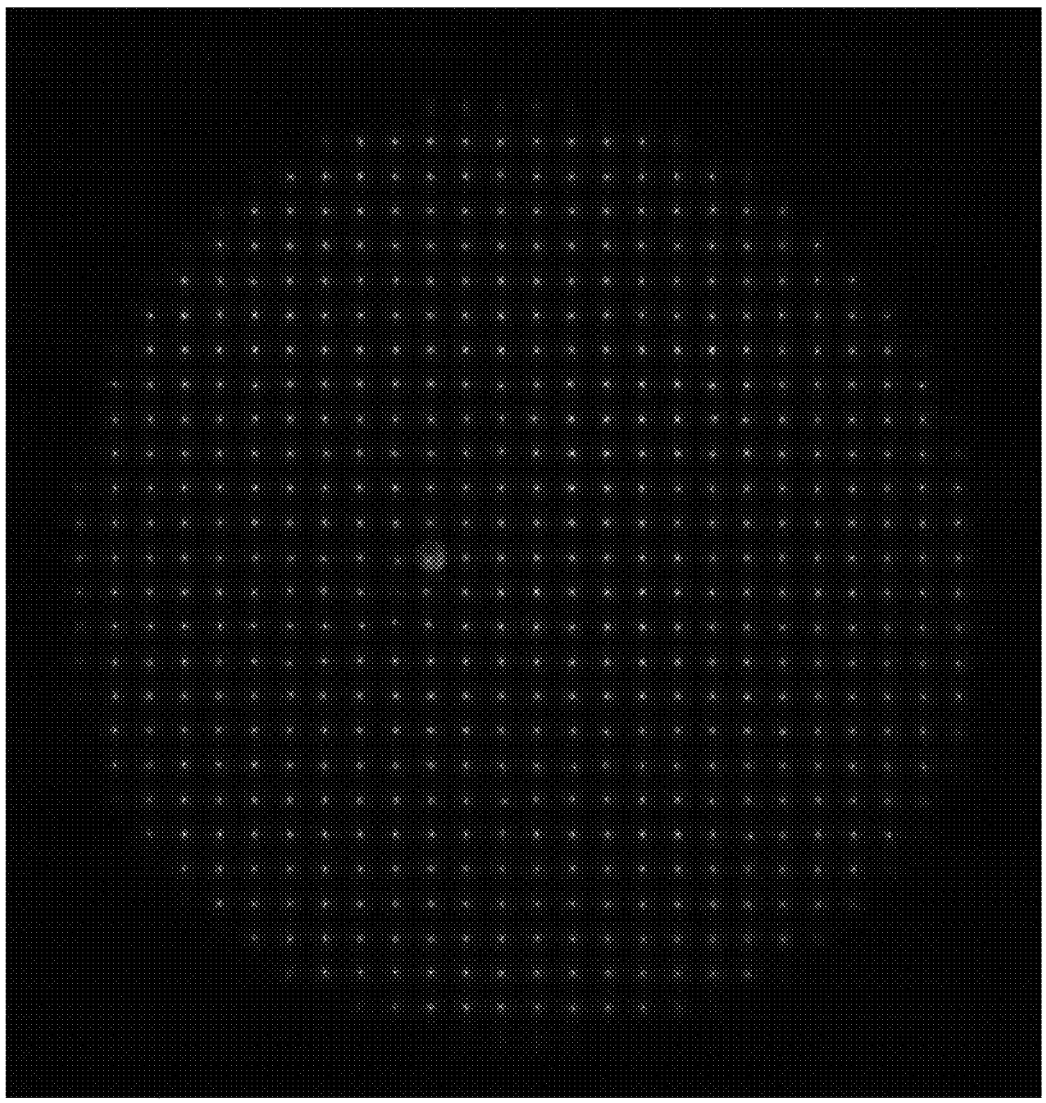
FIG. 11 shows a raw image from a wavefront sensor for a subject with a weak corneal reflex.

Disqualifications (or exclusions) of light spots affected by the various error sources described above can improve the quality of the waveform measurements. FIGS. 9-11 illustrate examples of various error cases.

FIG. 9 shows a raw image from a wavefront sensor for a subject with an intraocular lens. An IOL patient shows multiple corneal reflexes. Light spots affected by these multiple corneal reflexes may be disqualified or excluded from being employed in the wavefront measurements by calculating their locations through two different location calculation algorithms and comparing the differences in the locations obtained by the two algorithms to an agreement threshold, as explained in examples above.

FIG. 10 shows a raw image from a wavefront sensor for a subject with cataracts. Images from cataract patients often contain focal spots that are quite broad and dim because of the scattering in the lens. Again, these dim or misshapen light spots may be disqualified or excluded from being employed in the wavefront measurements by calculating their locations through two different location calculation algorithms and comparing the differences in the locations obtained by the two algorithms to an agreement threshold, as explained in examples above.

FIG. 11 shows a raw image from a wavefront sensor for a subject with a weak corneal reflex. Light spots affected by even this weak corneal reflex may be disqualified or excluded from being employed in the wavefront measurements by calculating their locations through two different location calculation algorithms and comparing the differences in the locations obtained by the two algorithms to an agreement threshold, as explained in examples above.

In the method 500 described above with respect to FIG. 5, light spots were also screened according to their summed intensity. In one embodiment, light spots whose summed intensities are less than a predetermined summed intensity threshold may be disqualified or excluded from being employed in the wavefront measurements.

Figure 12:
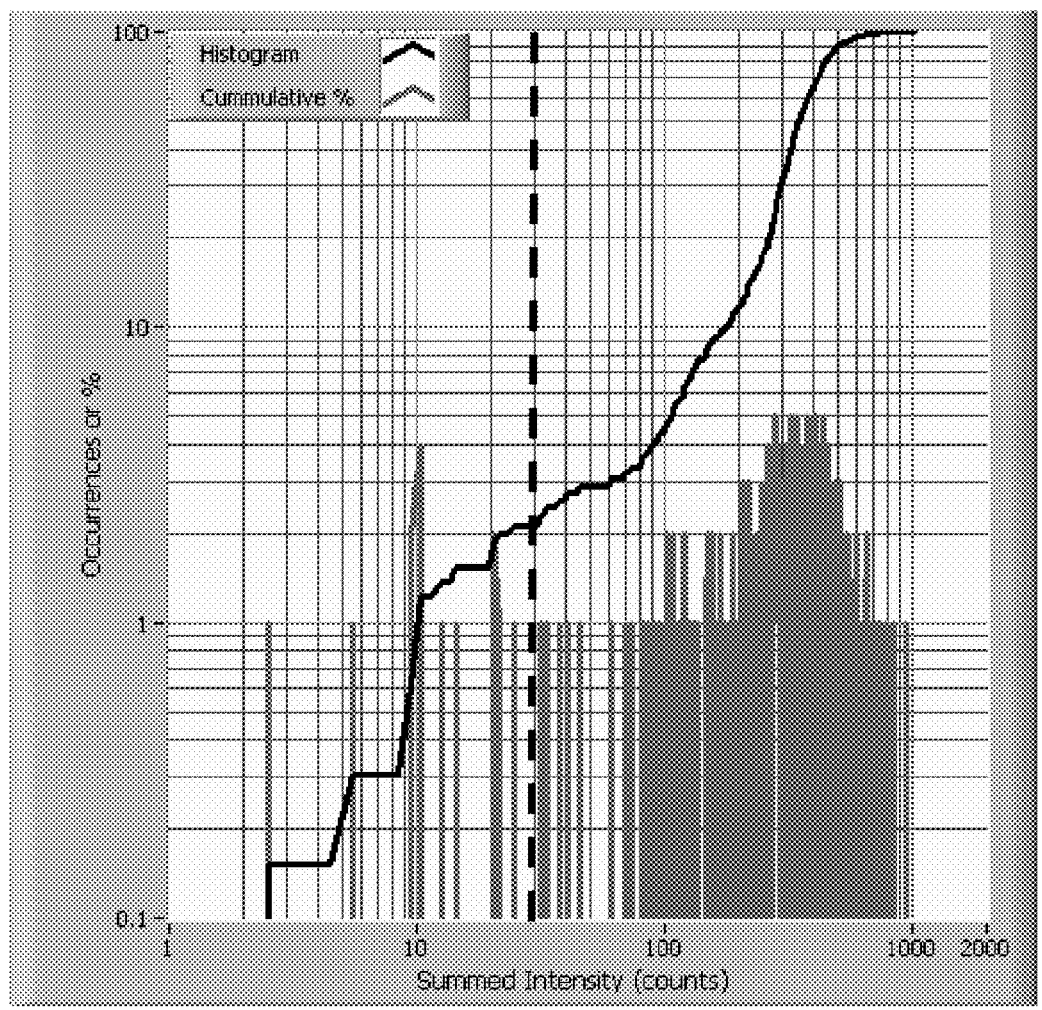
FIG. 12 is a histogram illustrating the summed intensity of pixels in a light spot as a function of occurrence for an exemplary image.

FIG. 12 is a histogram illustrating the summed intensity of pixels in a light spot as a function of occurrence for an exemplary image. From this data it is suggestive that a minimum summed intensity of around 30 counts will reject only about 2% of the light spots, most of which are from partially illuminated lenslets on the pupil boundary. Accordingly, in one embodiment the summed intensity threshold is set to 30.

Figures 13A, 13B:
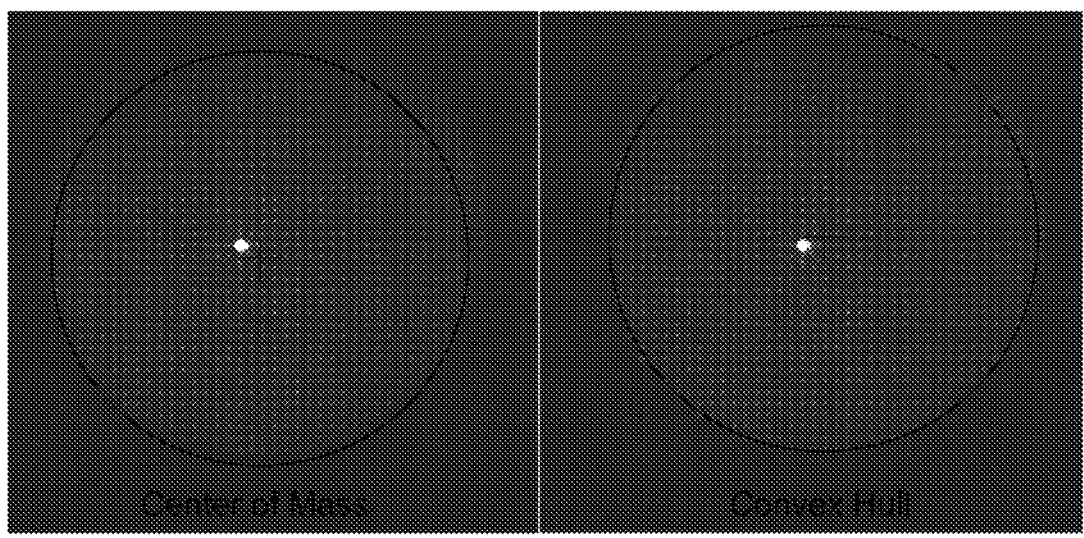
FIGS. 13A-B illustrate embodiments of two methods for determining the location and shape of a subject's pupil.

FIGS. 13A-B illustrate embodiments of two methods for determining the location and shape of a subject's pupil. An embodiment of a first pupil location determination method is based on a center of mass algorithm. An embodiment of a second pupil location determination method is based on a Convex Hull algorithm, using a priori knowledge that the boundary shape of the pupil should be generally circular, and mapping the light spots to match the expected boundary shape—where perhaps a portion of the pupil has been blocked or obscured. The pupil center and diameter are calculated using on the same light spot data using the two different methods. The data in FIGS. 13A-B show a case where the patient's eyelashes and/or eyelid partially obscure the wavefront data. The center of mass method is illustrated in FIG. 13A and leads to erroneous pupil center and diameter in this example. The Convex Hull algorithm illustrated in FIG. 13B minimizes the effects of eyelashes and blinking compared to center of mass algorithm. In FIGS. 13A-B, the cross and circle represent the results of each method. In one embodiment, a pupil location agreement threshold is set to 200 µm. In that case, the center of the pupil as calculated by both methods should agree to within 200 µm in order for the frame of data to be considered valid for wavefront measurement. Otherwise, the entire set of light spot data is discarded and a new image is employed for the wavefront measurement.

In an alternative arrangement, one of the two methods of determining the location and shape of the pupil may instead employ an image captured by an iris camera (e.g. iris camera 460 in FIG. 4) instead of the light spot data from the wavefront sensor.

Figure 14A:
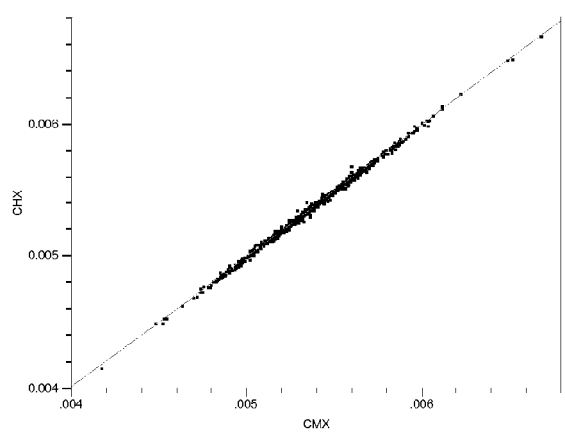
FIGS. 14A-B are plots illustrating the correlation of exemplary measurements made by the two methods illustrated in FIGS. 13A-B.
Figure 14B:
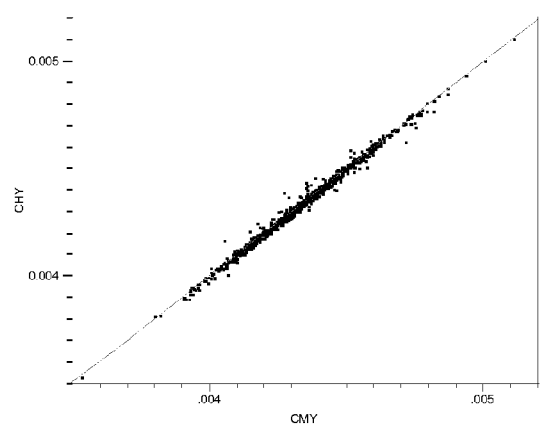

FIGS. 14A-B are plots illustrating the correlation of exemplary measurements made by the two Convex Hull and center of mass methods.

Figure 15:
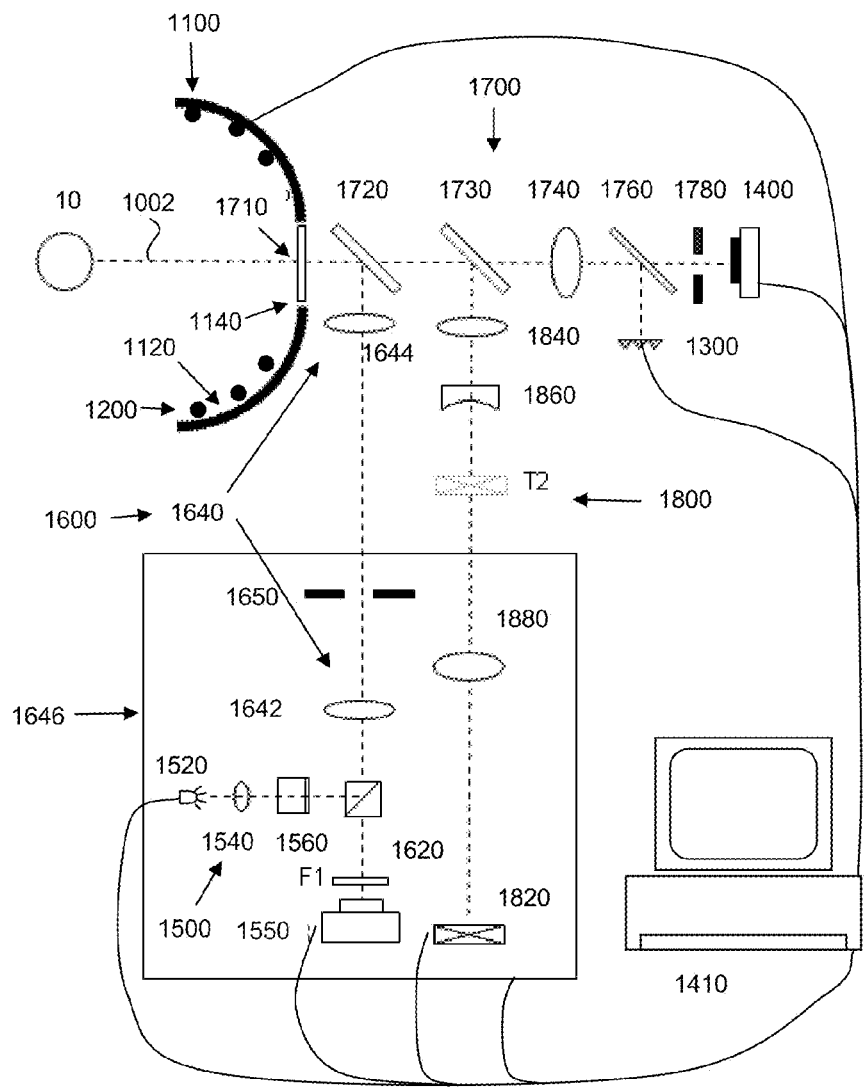
FIG. 15 shows one embodiment of a system for measuring wavefront aberrations and corneal topography of an eye.

FIG. 15 shows one embodiment of a system 1000 for measuring aberrations and the corneal topography of an eye 10. System 1000 comprises a structure 1100 having a principal surface 1120 with an opening or aperture 1140 therein; a plurality of first (or peripheral) light sources 1200 provided on the principal surface 1120 of the structure 1100; a plurality of second, or central, light sources 1300 (also sometimes referred to as "Helmholtz light sources"); a detector array 1400; a processor 1410; a third light source 1500 providing a probe beam; a wavefront sensor 1550; and an optical system 1700 disposed along a central axis 1002 passing through the opening or aperture 1140 of the structure 1100. Optical system 1700 comprises a quarterwave plate 1710, a first beamsplitter 1720, a second beamsplitter 1730, an optical element (e.g., a lens) 1740, a third beamsplitter 1760, and a structure including an aperture 1780. Beneficially, third light source 1500 includes a lamp 1520, a collimating lens 1540, and light source polarizing beamsplitter 1560. Associated with third light source 1500 and wavefront sensor 1550 in a wavefront analysis system 1600 also comprising: a polarizing beamsplitter 1620; an adjustable telescope 1640 comprising a first optical element (e.g., lens) 1642 and a second optical element (e.g., lens) 1644 and a movable stage or platform 1646; and a dynamic-range limiting aperture 1650 for limiting a dynamic range of light provided to wavefront sensor 1550. It will be appreciated by those of skill in the art that the lenses 1642, 1644, or any of the other lenses discussed herein, may be replaced or supplemented by another type of converging or diverging optical element, such as a diffractive optical element. Beneficially, system 1000 further comprises a fixation target system 1800, comprising light source 1820 and lenses 1840, 1860, and 1880.

Further details of system 1000 can be found by reference to U.S. Patent Application Publication 2009/0002631, filed in the names of Charles E. Campbell et al., and published on 1 Jan. 2009, the entirety of which is hereby incorporated herein by reference for all purposes as if fully set forth herein.

The operation of the topographer portion of system 1000 may be illustrated based on the combined use of first and second light sources 1200, 1300. In general, the images of first light sources 1200 that appear on detector array 1400 emanate from an outer region of the surface of the cornea, and the images of second light sources 1300 that appear on detector array 1400 emanate from a central or paraxial region of the surface of the cornea. Accordingly, even though information about the central region of the corneal surface (e.g., surface curvature) cannot be determined from the images of first light sources 1200 on detector array 1400, such information can be determined from the images of second light sources 1300 on detector array 1400.

Detector array 1400 detects the light spots projected thereon from both second light sources 1300 (detected at a central portion of detector array 1400) and first light sources 1200 (detected at a peripheral portion of detector array 1400) and provides corresponding output signals to processor 1410. Processor 1410 determines the locations and/or shapes of the light spots on detector array 1400, and compares these locations and/or shapes to those expected based for a standard or model cornea, thereby allowing processor 1410 to determine the corneal topography of eye 100. Accordingly, the topography of the entire corneal surface can be characterized by system 1000 without a "hole" or missing data from the central corneal region.

Data from the wavefront sensor 1550 may be analyzed using the method 500 described above.

Figure 16:
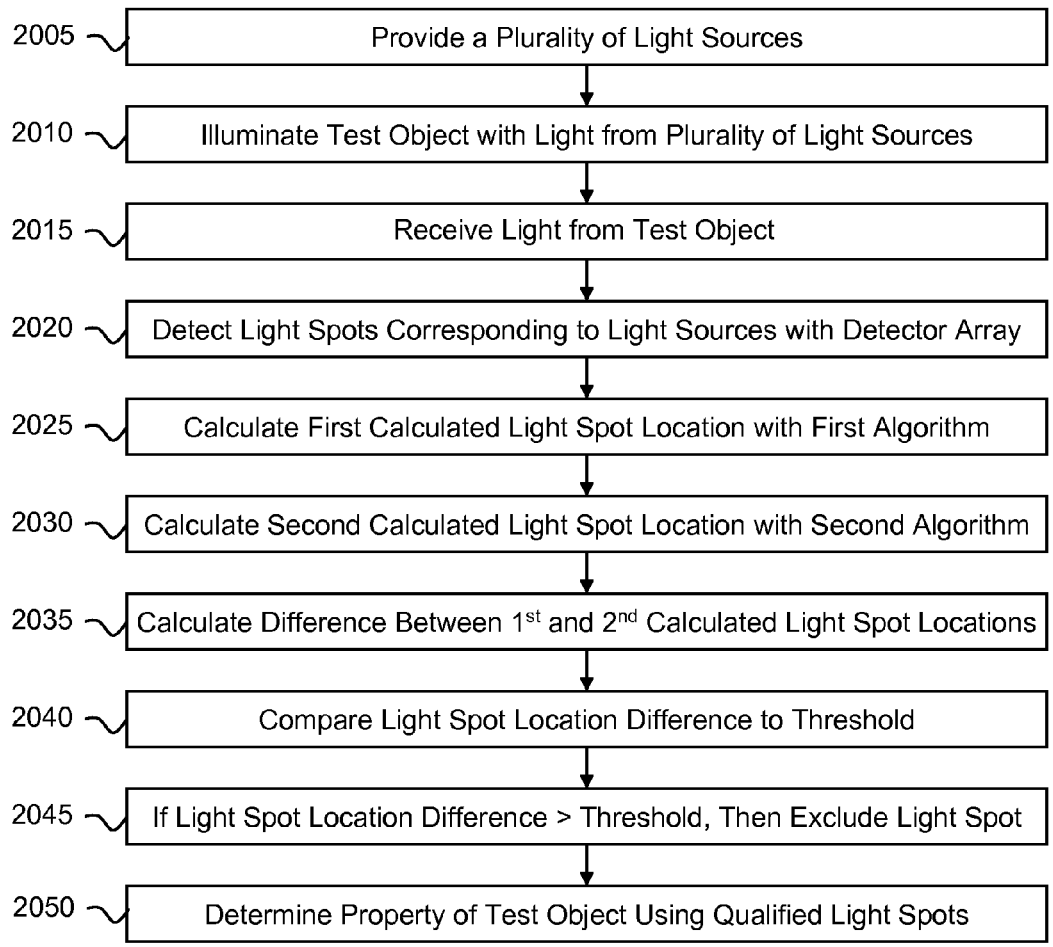
FIG. 16 shows a flowchart illustrating one embodiment of a method of qualifying light spot data for a corneal topography measurement.

FIG. 16 shows a flowchart illustrating one embodiment of a method 2000 of qualifying light spot data for a corneal topography measurement by an instrument such as corneal topographer portion of the system 1000 of FIG. 15. It will be appreciated that the method 2000 may be adapted, and modified as appropriate, to analyze data for other topographer systems used to measure the topography of a cornea or the surface profile of some other test object, such as a test mirror or lens.

In a first step 2005, a plurality of light sources is provided.

In a step 2010, a test object (e.g., the cornea of the eye 10 for the system 1000) is illuminated with light from the plurality of light sources.

In a step 2015, light that has illuminated the test object is provided to an optical system.

In a step 2020, a group of light spots corresponding to the light sources are produced on a detector array.

Next, a set of the light spots are qualified.

In a step 2025, a processor calculates a first calculated location of each light spot using a first calculation algorithm.

In a step 2030, a processor calculates a second calculated location of each light spot using a second calculation algorithm different from the first calculation algorithm.

In a step 2035, the processor calculates a difference between the first and second calculated locations.

In a step 2040, the processor compares the difference between the first and second calculated locations for the light spot, to a predetermined agreement threshold.

In a step 2045, the processor excludes from a qualified set of light spots those light spots where the difference between the first and second calculated locations is greater than the agreement threshold. The qualified set of spots is employed in determining a property of the eye 100, for example, a surface shape of the cornea of the eye 10.

In a step 2050 a property of the test object is determined using the qualified set of light spots.

In certain embodiments, the method 2000 may include additional steps. For example, for the purposes of determining the property of the test object, the qualified spots may be assigned a weighting depending on an evaluation criteria. Additionally or alternatively, some or all of the light spots excluded from the set of qualified light spots may be further evaluated or processed. For example, some or all of the excluded light spots may be evaluated for inclusion in a second set of light spots. In such embodiments, the step 2050 of method 2000 may include the second set of light spots in determining the property of the test object, for example, by assigning a reduced weight in calculating the wavefront as compared to the weight or weights given to spots in the qualified set.

Additionally or alternatively, the second set of light spots may be used to detect a condition of the test object (e.g., a cataract or dry eye condition or chronic dry eye condition when the test object is the eye 10) and/or form the basis of a qualitative or quantitative characterization of the mechanisms that caused the disqualification. For example, the location, severity, and/or extent of tear film breakup may be measured or estimated based on the second set of light spots. Additionally or alternatively, the location and severity of larger local surface anomalies of a cornea surface caused by large corneal surface deviation may be measured or estimated based on the second set of light spots.

In certain embodiments, data from both the wavefront sensor 1550 of system 1000 and the topographer portion of system 1000 may be used together to qualify data from one system and/or the other.

Figure 17:
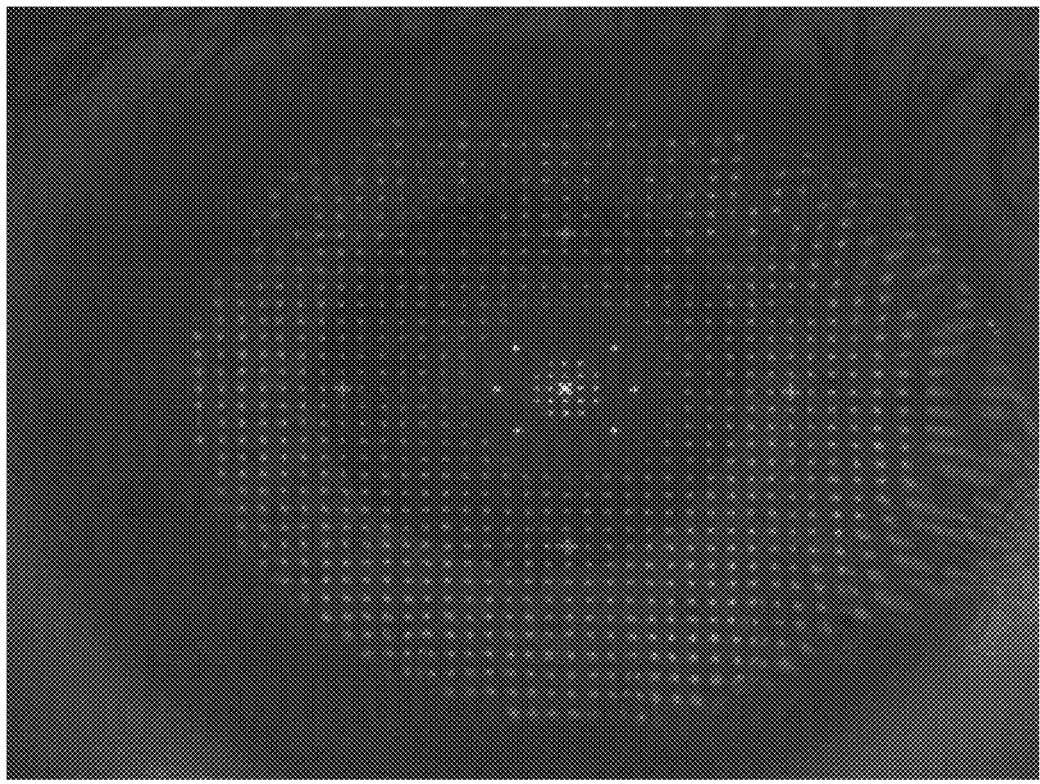
FIG. 17 shows an exemplary topographic image of an eye.
Figure 18:
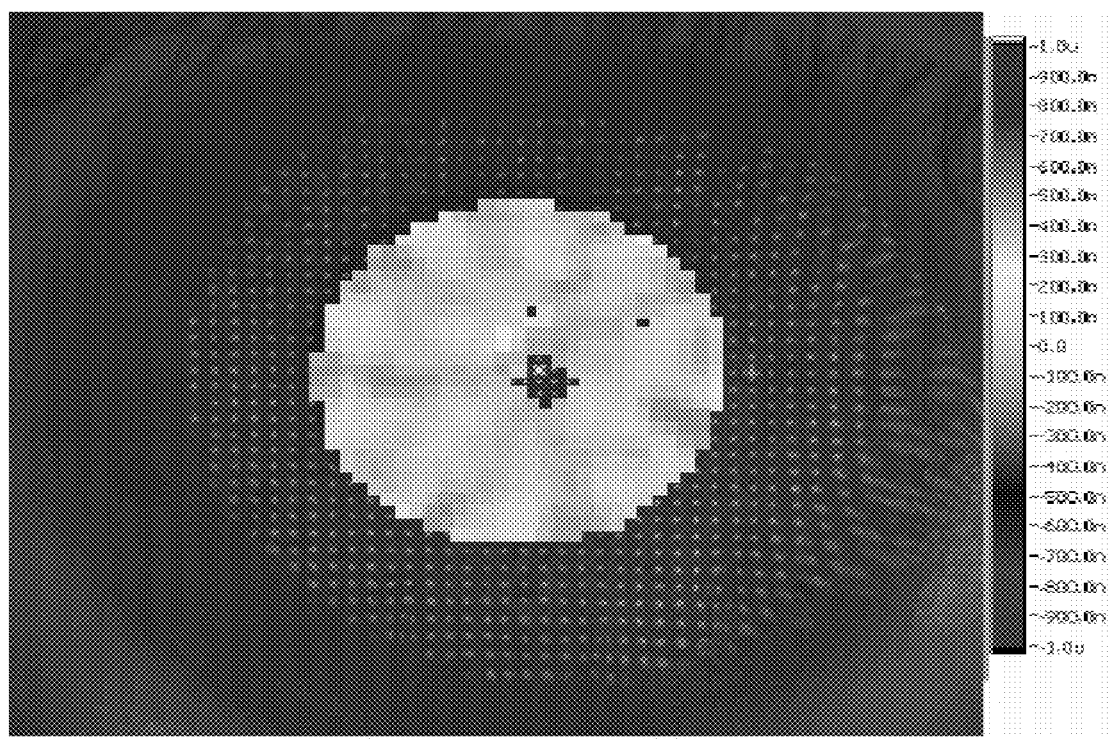
FIG. 18 shows exemplary wavefront data for an eye superimposed on a topographic image of the eye.

For example, FIG. 17 shows an exemplary topographic image of an eye produced from the corneal topographer portion of system 1000. FIG. 18 shows exemplary wavefront data of the same eye from wavefront sensor 1550 of system 1000, superimposed on top of the topographic image of FIG. 17. In this case, the data from both the wavefront sensor and topographer is generally well behaved and both may be used to provide validated measurements of the eye.

Figure 19:
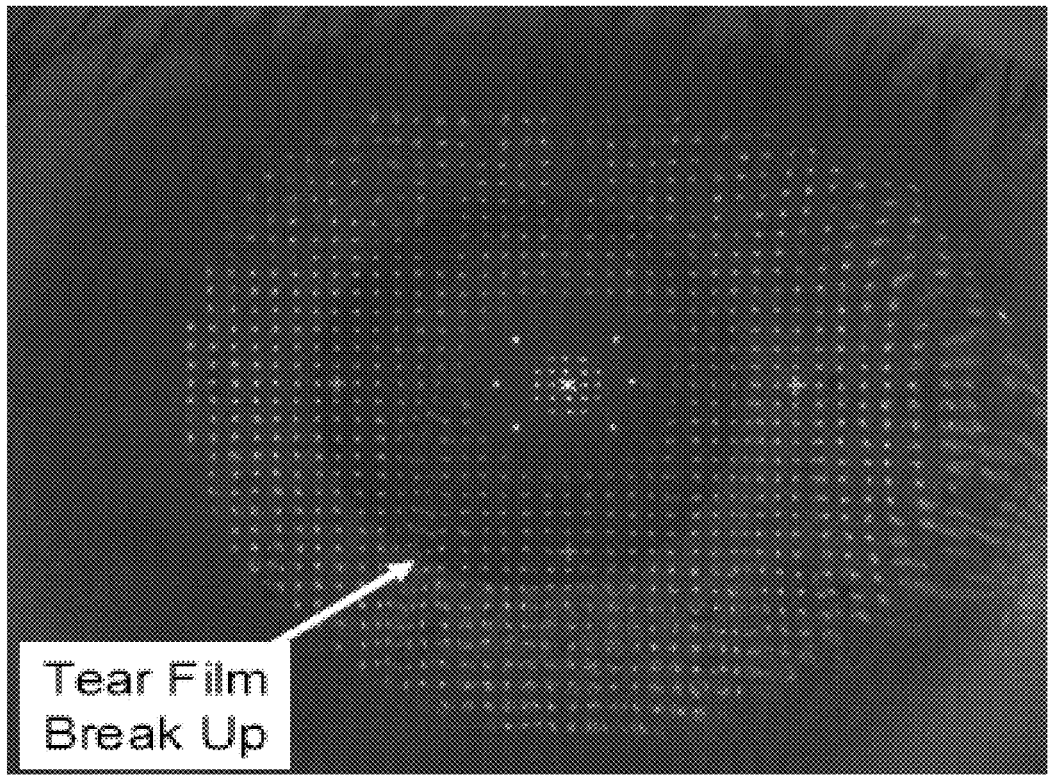
FIG. 19 shows an exemplary topographic image of an eye under a condition of tear film breakup.
Figure 20:
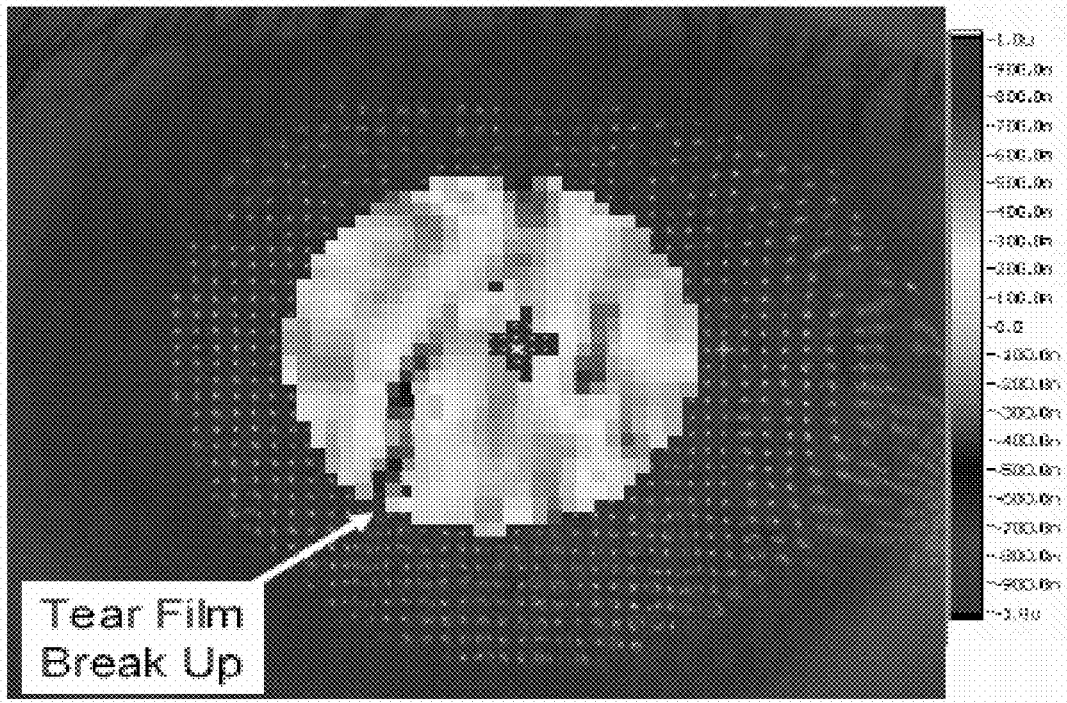
FIG. 20 shows exemplary wavefront data for an eye superimposed on a topographic image of the eye under a condition of tear film breakup.

In contrast, FIG. 19 shows another exemplary topographic image of the same eye using the system 1000 is shown, where the blurred spot images in the bottom portion of the image give clear indication of the presences, severity, and extent of the tear film breakup due to a dry eye or chronic dry eye condition. FIG. 20 shows exemplary wavefront data from the wavefront sensor 1550 that is superimposed on top of the topographer image of FIG. 19 for the same eye under the same conditions. In this case, the wavefront data is still fairly well behaved, with only a few data points (dark squares within the generally circular wavefront data image) being disqualified. However, based on the topographic image in FIG. 19, all or portions of the wavefront data shown in FIG. 20 may be disqualified based on the tear film breakup indicated from the topographer data shown in FIG. 19. Thus, the image from a corneal topography measurement may be used to modify or eliminate data provided by the wavefront sensor alone.

Figure 21:
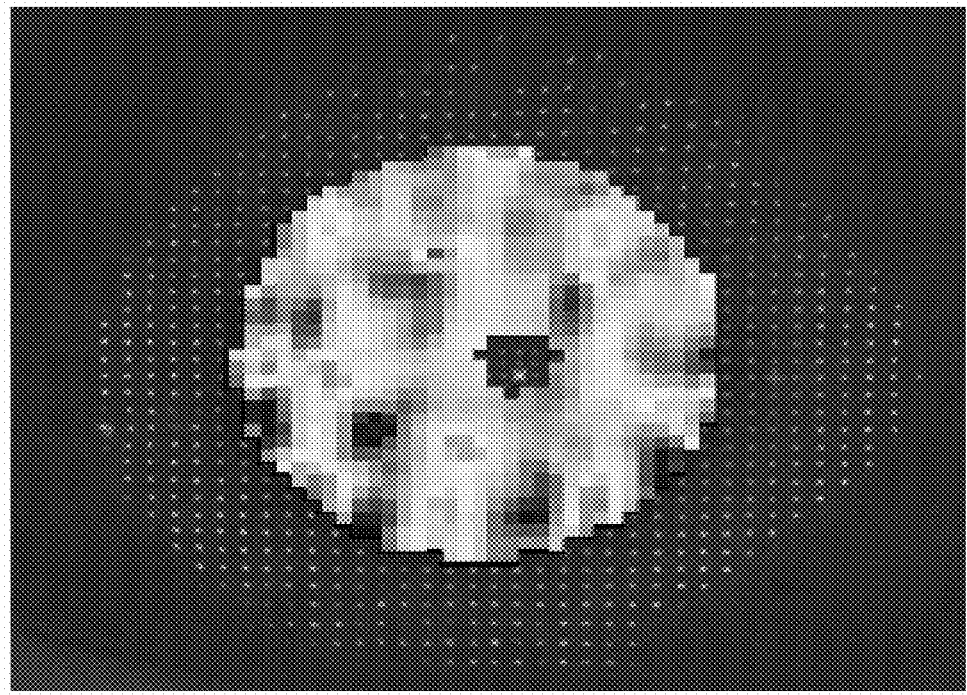
FIG. 21 shows another example of wavefront data for an eye superimposed on a topographic image of the eye

FIG. 21 is another illustration of exemplary wavefront data from the wavefront sensor 1550 that is superimposed on top of a topographic image for an eye taken under the same conditions (e.g., at the same time). FIG. 21 illustrates an opposite case to that explained above with respect to FIGS. 19 and 20. In other words, in FIG. 21, the corneal topography image appears to be normal, but the wavefront data is mottled. In this case, the wavefront data may be used to modify or eliminate data provided by the corneal topographer alone.

Figure 22:
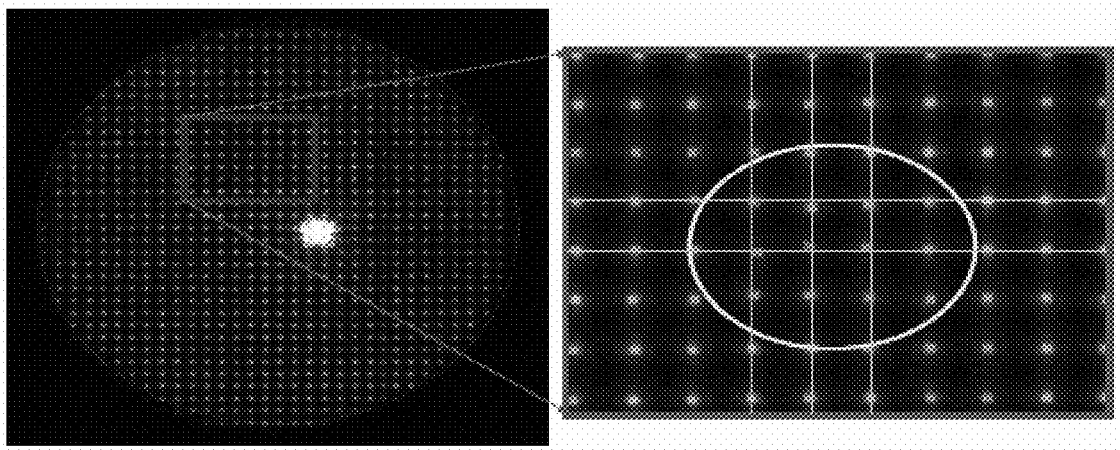
FIG. 22 shows wavefront data for an eye with an anomalous condition.

FIG. 22 shows data from the wavefront sensor 1550 for a condition in which the light spots in one region of the eye have relatively large deviations from a nominal condition. This anomalous region of the eye is indicated by the square in the overall light spot image shown on the left side of FIG. 22. A magnified view of this region is shown in the box on the right side of FIG. 22. The nominal light spot positions are indicated by the lined grid in the magnified view. As can be seen in the magnified view, many of the light spots within the enclosed area have visibly large deviations compared to the other light spots outside the enclosed area. In this case, the topography light spot for the same region of the eye showed relatively small deviations that were within expected nominal values for a typical cornea. Thus, the large deviations within the wavefront data in FIG. 22 could not be accounted for by corneal aberrations or an anomalous surface profile. Therefore, the source of the large deviations in FIG. 22 had to come from abnormality within the eye, for example due to the presence of a cataract within the natural lens. Thus, a comparison of the wavefront data in FIG. 22 with the corresponding topographer data may be used to detect or determine an abnormality of the eye, such as the presence of a cataract.

Figure 23:
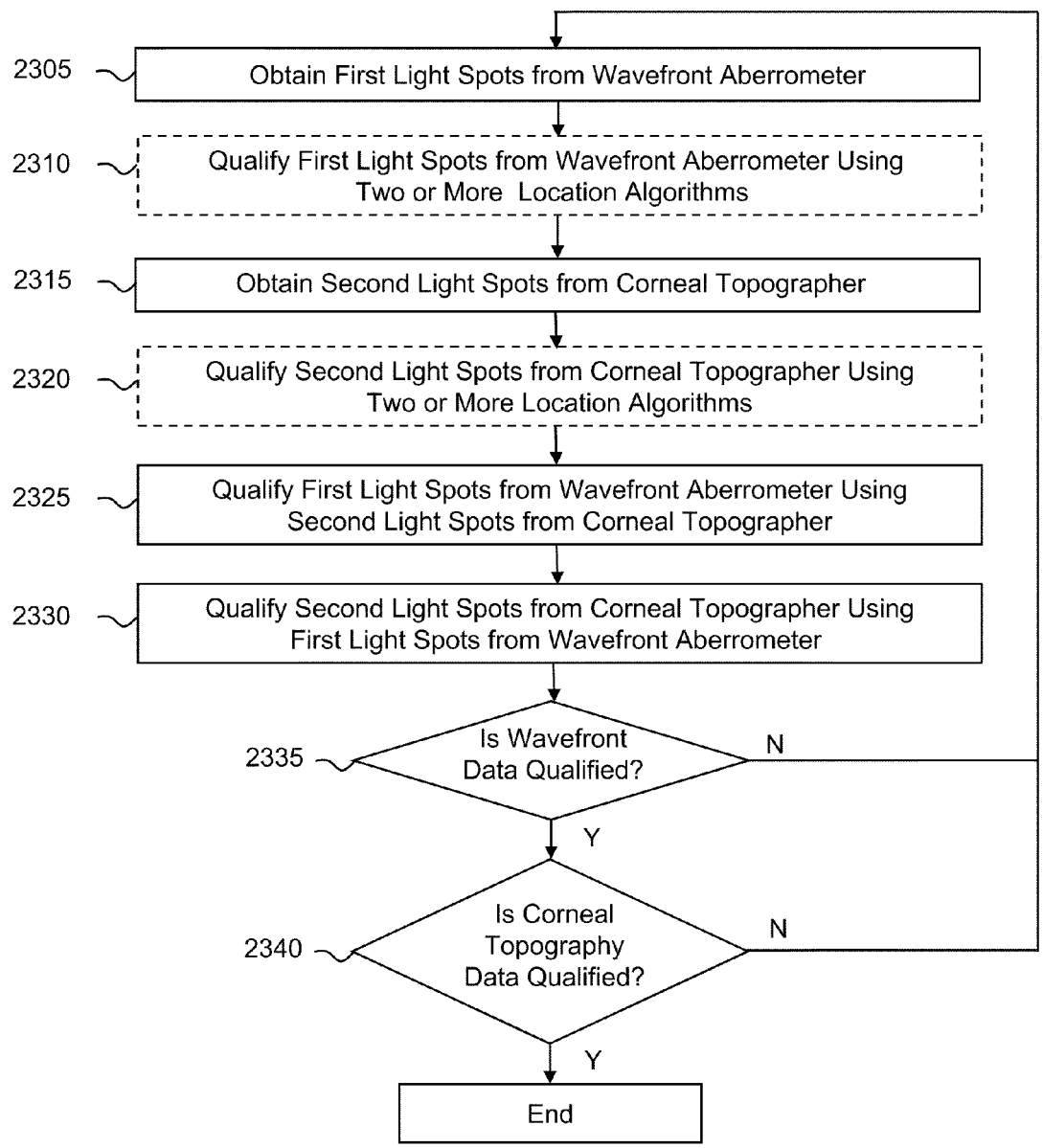
FIG. 23 shows a flowchart illustrating one embodiment of a method of making a wavefront measurement and a corneal topography measurement of an eye.

FIG. 23 shows a flowchart illustrating one embodiment of a method 2300 of performing a wavefront measurement and a corneal topography measurement of an eye. In one embodiment, method 2300 may be performed by a system such as the system 1000 illustrated in FIG. 15.

In a first step 2305, a first set of light spots are obtained from a wavefront aberrometer such as the wavefront aberrometer of the system 1000 of FIG. 15. In one embodiment, step 2305 may include steps 505-510 of method 500 described above.

In an optional step 2310, the first light spots comprising wavefront data may be qualified to produce a first qualified set of light spots. In one embodiment, step 2310 may include steps 515-540 of method 500 described above.

In a step 2315, a second set of light spots are obtained from a corneal topographer instrument such as corneal topographer portion of the system 1000 of FIG. 15. In one embodiment, step 2305 may include steps 2005-2020 of method 2000 described above. Beneficially, step 2315 is performed at a same time as step 2305. That is, beneficially the corneal topography image of an eye produced by step 2315 is taken at the same time that the wavefront data for the same eye is produced by step 2305.

In a step 2320, the second light spots may be qualified to produce a second qualified set of light spots. In one embodiment, step 2310 may include steps 2025-2045 of method 2000 described above. In one embodiment, step 2310 may include steps 2025-2045 of method 2000 described above.

In a step 2325, the first light spots from the wavefront aberrometry measurement are qualified by the image formed by the second light spots produced by the corneal topography measurement. The first light spots and/or the second light spots employed in step 2325 may be qualified by step 2310 and/or step 2320 as described above. An example of qualifying the wavefront light spots by a corneal topography image is described above with respect to FIGS. 17-20.

In a step 2330, the second light spots from the corneal topography measurement are qualified by the image formed by the first light spots produced by the wavefront aberrometry measurement. The first light spots and/or the second light spots employed in step 2330 may be qualified by step 2310 and/or step 2320 as described above. An example of qualifying the topography light spots by wavefront data is described above with respect to FIG. 21.

In a step 2335, a determination is made as to whether the light spots from the wavefront measurement should be disqualified, based on its comparison to the corneal topography data. For example, if too many of the light spots from the wavefront are disqualified based on the corresponding corneal topography data, the entire set of wavefront data may be disqualified from use. Additionally, or alternatively, if the corneal topography data indicates the presence of a condition such as tear film breakup, the entire set of wavefront data may be disqualified from use. In that case, the process returns to step 2305 and new data is captured.

In a step 2340, a determination is made as to whether the light spots from the corneal topography measurement should be disqualified, based on its comparison to the wavefront data. For example, if too many of the light spots from the corneal topography measurement are disqualified based on the corresponding wavefront data, the entire set of corneal topography data may be disqualified from use. Additionally, or alternatively, if the wavefront data indicates the presence of an anomalous condition, the entire set of corneal topography data may be disqualified from use. In that case, the process returns to step 2305 and new data is captured.

A clinical study was performed using a system similar to the system 1000—a system containing both a wavefront aberrometer and corneal topographer. The study specifically looked at wavefront aberrometer and topography data for measuring astigmatism in a population of subject eyes. Based on wavefront aberrometer and topography data from the population, the inventors made various observations. Corneal and wavefront aberrations are weakly correlated for the entire population. For eyes with manifest refraction less than 1D there is no correlation between corneal and total wavefront aberration. For eyes with manifest astigmatism greater than 1D, the correlation is stronger and about 80% of the aberration can be attributed to the cornea. By examining combined corneal and wavefront data the source of wavefront aberration can be attributed to the cornea or other ocular components.

While preferred embodiments are disclosed herein, many variations are possible which remain within the concept and scope of the invention. Such variations would become clear to one of ordinary skill in the art after inspection of the specification, drawings and claims herein. The invention therefore is not to be restricted except within the spirit and scope of the appended claims.

We claim:

1. A method of employing an optical sensor to determine a property of an object, the method comprising:
   (a) illuminating the object with light from one or more light sources;
   (b) receiving light from the illuminated object;
   (c) producing a group of light spots from the received light;
   (d) qualifying a set of the light spots for use in determining a property of the object; and
   (e) determining the property of the object using the qualified set of light spots,
   wherein qualifying the set of light spots includes, for each light spot in the group of light spots:
      calculating a first calculated location of the light spot using a first calculation algorithm;
      calculating a second calculated location of the light spot using a second calculation algorithm different from the first calculation algorithm; and
      when a difference between the first and second calculated locations for the light spot is greater than an agreement threshold, excluding the light spot from the qualified set of light spots.

2. The method of claim 1, wherein the optical sensor includes a detector array having a plurality of pixels, and wherein qualifying the set of light spots further comprises, for each light spot not already excluded from the qualified set of light spots, determining a summed intensity value of an assigned group of pixels of the detector array assigned to the light spot and excluding from the qualified set of light spots any light spot whose summed intensity is less than a summed intensity threshold.

3. The method of claim 1, wherein the optical sensor includes a wavefront sensor and qualifying the set of light spots further comprises:
   determining a difference between a first determined location of a pupil of an eye as determined from a sensed wavefront according to a first method, and a second determined location of the pupil determined from a second method different from the first method; and
   when a difference between the first determined location and the second determined location is greater than a pupil location agreement threshold, then excluding all of the of light spots in the group of light spots and repeating steps (a) through (d) for a new group of light spots before performing step (e).

4. The method of claim 1, wherein qualifying the set of light spots further comprises:
   determining a size of a largest cluster of light spots that have been excluded so far from the qualified set of light spots; and
   when the size of a largest cluster of light spots that have been excluded from the qualified set of light spots so far is greater than a cluster size threshold, then excluding all of the of light spots in the group of light spots and repeating steps (a) through (d) for a new group of light spots before performing step (e).

5. The method of claim 1, wherein the optical sensor includes a detector array having a plurality of pixels, and wherein calculating the first calculated location for each light spot using the first calculation algorithm comprises, for each light spot:
   assigning a group of the pixels to the light spot;
   establishing a pixel intensity threshold for the light spot;
   determining an intensity value for light received at each pixel in the group; and
   calculating the first calculated location as a first moment of the pixel intensity values for those pixels whose intensity values are greater than the pixel intensity threshold.

6. The method of claim 5, wherein establishing the pixel intensity threshold for the light spot comprises:
   establishing a background intensity threshold value that is constant for all light spots;
   determining a maximum intensity value among the intensity values for all of the pixels in the group;
   establishing a percentage threshold value for the light spot; and
   establishing the pixel intensity threshold by multiplying the percentage threshold value by the maximum intensity value and subtracting the background intensity threshold value.

7. The method of claim 5, wherein calculating the second calculated location for each light spot using the second calculation algorithm comprises:
   determining a brightest pixel having a maximum intensity value among the intensity values for light received at all of the pixels in the group;
   establishing a spatial window surrounding the brightest pixel;
   setting a window threshold equal to the maximum intensity value among the intensity values for pixels located on a border of the spatial window; and
   calculating the second calculated location as a first moment of the pixel intensity values for those pixels whose intensity values are greater than the window threshold.

8. The method of claim 1, wherein the optical sensor includes a detector array having a plurality of pixels, and wherein calculating the second calculated location for each light spot using the second calculation algorithm comprises:
   assigning a group of the pixels to the light spot;
   determining an intensity value for light received at each pixel in the group
   determining a brightest pixel having a maximum intensity value among the intensity values for light received at all of the pixels in the group;
   establishing a spatial window surrounding the brightest pixel;
   setting a window threshold equal to the maximum intensity value among the intensity values for pixels located on a border of the spatial window; and calculating the second calculated location as a first moment of the pixel intensity values for those pixels whose intensity values are greater than the window threshold.

9. The method of claim 1, wherein the light received from the illuminated object is light that is reflected by the object.

10. The method of claim 1, wherein the light received from the illuminated object is light that is transmitted through the object.

11. A device comprising:
one or more light sources for illuminating an object;
a light spot generator adapted to receive light from the illuminated objected and to generate a group of light spots from the light received from the illuminated object;
a detector adapted to detect the light spots and for outputting light spot data pertaining to each light spot; and
a processor adapted to process the light spot data to determine a property of the object by:
qualifying a set of the light spots for use in determining the property, and
determining the property of the object using the qualified set of light spots,
wherein qualifying the set of light spots includes, for each light spot in the group of light spots:
calculating a first calculated location of the light spot from the light spot data using a first calculation algorithm;
calculating a second calculated location of the light spot from the light spot data using a second calculation algorithm different from the first calculation algorithm; and
when a difference between the first and second calculated locations for the light spot is greater than an agreement threshold, excluding the light spot from the qualified set of light spots.

12. The device of claim 11, wherein qualifying the set of light spots further comprises, for each light spot not already excluded from the set of light spots, assigning a quality value to the light spot and excluding from the set of light spots any light spot whose quality value is less than a predetermined threshold.

13. The device of claim 11, wherein qualifying the set of light spots further comprises, for each light spot not already excluded from the set of light spots, determining a summed intensity of the light spot from the light spot data and excluding from the set of light spots any light spot whose summed intensity is less than a summed intensity threshold.

14. The device of claim 13, wherein the detector comprises an array of pixels, and wherein determining the summed intensity of a light spot comprises:
assigning a group of the pixels to the light spot;
determining an intensity value for light received at each pixel in the group from the light spot data; and
adding the pixel intensity values to determine the summed intensity of the light spot.

15. The device of claim 11, wherein device includes a wavefront sensor, and wherein qualifying the set of light spots further comprises:
determining a difference between a first determined location of a pupil of an eye as determined from a sensed wavefront according to a first method, and a second determined location of the pupil determined from a second method different from the first method; and
when the difference between the first determined location and the second determined location is greater than a pupil location agreement threshold, then excluding all of the of light spots in the group of light spots, obtaining new light spot data from a new group of light spots, and processing the new light spot data.

16. The device of claim 11, wherein qualifying the set of light spots further comprises:
determining a size of a largest cluster of light spots that have been excluded so far from the qualified set of light spots; and
when the size of a largest cluster of light spots that have been excluded so far from the qualified set of light spots is greater than a cluster size threshold, then excluding all of the of light spots in the group of light spots, obtaining new light spot data from a new group of light spots, and processing the new light spot data.

17. The device of claim 11, wherein the detector comprises an array of pixels, and wherein calculating the first calculated location for each light spot using the first calculation algorithm comprises:
assigning a group of the pixels to the light spot;
establishing a pixel intensity threshold for the light spot;
determining an intensity value for light received at each pixel in the group; and
calculating the first calculated location as a first moment of the pixel intensity values for those pixels whose intensity values are greater than the pixel intensity threshold.

18. The device of claim 17, wherein establishing the pixel intensity threshold for the light spot comprises:
establishing a background intensity threshold value that is constant for all light spots;
determining a maximum intensity value among the intensity values for all of the pixels in the group;
establishing a percentage threshold value for the light spot; and
establishing the pixel intensity threshold by multiplying the percentage threshold value by the maximum intensity value and subtracting the background intensity threshold value.

19. The device of claim 17, wherein calculating the second calculated location for each light spot using the second calculation algorithm comprises:
determining a brightest pixel having a maximum intensity value among the intensity values for light received at all of the pixels in the group;
establishing a spatial window surrounding the brightest pixel;
setting a window threshold equal to the maximum intensity value among the intensity values for pixels located on a border of the spatial window
calculating the second calculated location as a first moment of the pixel intensity values for those pixels whose intensity values are greater than the window threshold.

20. The device of claim 11, wherein the detector comprises an array of pixels, and wherein calculating the second calculated location for each light spot using the second calculation algorithm comprises:
assigning a group of the pixels to the light spot;
determining an intensity value for light received at each pixel in the group
determining a brightest pixel having a maximum intensity value among the intensity values for light received at all of the pixels in the group;
establishing a spatial window surrounding the brightest pixel;
setting a window threshold equal to the maximum intensity value among the intensity values for pixels located on a border of the spatial window; and calculating the second calculated location as a first moment of the pixel intensity values for those pixels whose intensity values are greater than the window threshold.

21. The device of claim 11, wherein the device includes a wavefront sensor, and wherein the property is a characteristic of a wavefront of the light produced by the object and received by the light spot generator.

22. The device of claim 11, wherein the device includes a topographer and the property is a shape of the object.

23. A method, comprising:
   producing a first set of first light spots from an eye with a corneal topography measurement;
   producing a second set of second light spots from the eye with a wavefront aberrometry measurement; and
   qualifying one or more of the light spots within one of the first and second set of light spots based on the other of the first and second set of light spots.

24. The method of claim 23, wherein the first set of first light spots is a qualified set of first light spots, and wherein producing the first set of light spots from the eye with the corneal topography measurement includes:
   (a) providing a plurality of light sources;
   (b) illuminating the eye with light from the plurality of light sources;
   (c) receiving light that has illuminated the eye;
   (d) producing a group of first light spots from the received light; and
   (e) qualifying at least some of the group of first light spots to produce the first set of first light spots.

25. The method of claim 24, wherein qualifying a set of the first light spots to produce the first set of first light spots comprises, for each first light spot in the group of first light spots:
   calculating a first calculated location of the first light spot using a first calculation algorithm;
   calculating a second calculated location of the first light spot using a second calculation algorithm different from the first calculation algorithm; and
   when a difference between the first and second calculated locations for the first light spot is less than an agreement threshold, qualifying the first light spot, and otherwise, disqualifying the first light spot.

26. The method of claim 23, wherein the second set of second light spots is a qualified set of second light spots, and wherein producing the second set of light spots from the eye with the wavefront aberrometry measurement includes:
   (a) receiving a light beam from the eye;
   (b) producing a group of second light spots from the light beam; and
   (c) qualifying a set of the second light spots to produce the second set of second light spots.

27. The method of claim 26, wherein qualifying a set of the second light spots to produce the second set of second light spots comprises, for each second light spot in the group of second light spots includes:
   calculating a first calculated location of the second light spot using a first calculation algorithm;
   calculating a second calculated location of the second light spot using a second calculation algorithm different from the first calculation algorithm; and
   when a difference between the first and second calculated locations for the second light spot is less than an agreement threshold, qualifying the second light spot, and otherwise, disqualifying the second light spot.

* * * * *